United States Patent
Brill et al.

(10) Patent No.: US 11,173,308 B2
(45) Date of Patent: Nov. 16, 2021

(54) VIRTUAL TARGET POLE ADJUSTMENT BASED ON NERVE ROOT TRAJECTORY

(71) Applicant: Boston Scientific Neuromodulation Corporation, Valencia, CA (US)

(72) Inventors: Natalie Brill, Sherman Oaks, CA (US); Rosana Esteller, Santa Clarita, CA (US); Jessica Block, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 58 days.

(21) Appl. No.: 16/289,047

(22) Filed: Feb. 28, 2019

(65) Prior Publication Data

US 2019/0269919 A1  Sep. 5, 2019

Related U.S. Application Data

(60) Provisional application No. 62/638,786, filed on Mar. 5, 2018.

(51) Int. Cl.
*A61N 1/36* (2006.01)
*A61N 1/05* (2006.01)
(Continued)

(52) U.S. Cl.
CPC ............ *A61N 1/36071* (2013.01); *A61B 5/24* (2021.01); *A61N 1/0551* (2013.01);
(Continued)

(58) Field of Classification Search
CPC ............ A61N 1/36071; A61N 1/36062; A61N 1/0551; A61N 1/3605; A61N 1/37247; A61N 1/37264; A61B 5/04001
See application file for complete search history.

(56) References Cited

U.S. PATENT DOCUMENTS 5,814,092 A  9/1998 King
6,078,838 A  6/2000 Rubinstein
(Continued)

FOREIGN PATENT DOCUMENTS

EP  2709721  9/2016
WO  2006/029090  3/2006
(Continued)

OTHER PUBLICATIONS

E.L. Air et al., "Electrophysiologic Monitoring for Placement of Laminectomy Leads for Spinal Cord Stimulation Under General Anesthesia," Neuromodulation: Technology at the Neural Interface, vol. 15(6), pp. 573-580 (2012).
(Continued)

*Primary Examiner* — Ankit D Tejani
*Assistant Examiner* — Joshua Brendon Solomon
(74) *Attorney, Agent, or Firm* — Lewis & Reese, PLLC

(57) ABSTRACT

Techniques for determining the trajectory of a one or more dorsal roots and utilizing the trajectories to improve a spinal cord stimulation model are disclosed. A first improvement constructs a target stimulation field along a path that is parallel with the determined trajectory that is nearest to a specified desired location of stimulation. An allocation of stimulation among the electrodes to mimic the target field is computed. A second improvement models a response of neural elements at evaluation positions that are parallel with the trajectories based on the electric field that is generated for the computed allocation of stimulation among the electrodes. The stimulation amplitude is adjusted based on the neural element modeling to maintain stimulation intensity, and the stimulation amplitude and allocation of stimulation among the electrodes are compiled into an electrode configuration that is communicated to a neurostimulator.

20 Claims, 17 Drawing Sheets

(51) Int. Cl.
*A61N 1/372* (2006.01)
*A61B 5/24* (2021.01)

(52) U.S. Cl.
CPC ....... *A61N 1/3605* (2013.01); *A61N 1/36062* (2017.08); *A61N 1/37247* (2013.01); *A61N 1/37264* (2013.01)

(56) References Cited

U.S. PATENT DOCUMENTS

| | | |
|---|---|---|
| 6,516,227 B1 | 2/2003 | Meadows et al. |
| 6,718,210 B1 | 4/2004 | Peckham et al. |
| 6,907,130 B1 | 6/2005 | Rubinstein et al. |
| 7,890,182 B2 | 2/2011 | Parramon et al. |
| 8,335,569 B2 | 12/2012 | Aghassian |
| 8,412,345 B2 | 4/2013 | Moffitt |
| 8,463,400 B2 | 6/2013 | Hegi et al. |
| 8,498,716 B2 | 7/2013 | Chen et al. |
| 8,594,797 B2 | 11/2013 | Lee |
| 8,606,362 B2 | 12/2013 | He et al. |
| 8,620,436 B2 | 12/2013 | Parramon et al. |
| 8,644,947 B2 | 2/2014 | Zhu et al. |
| 8,768,453 B2 | 7/2014 | Parramon et al. |
| 8,798,759 B2 | 8/2014 | Goetz et al. |
| 8,812,124 B2 | 8/2014 | Lee |
| 8,825,169 B2 | 9/2014 | Zhu et al. |
| 8,909,350 B2 | 12/2014 | Lee |
| 8,913,804 B2 | 12/2014 | Blum et al. |
| 9,014,820 B2 | 4/2015 | Lee et al. |
| 9,061,140 B2 | 6/2015 | Shi et al. |
| 9,119,964 B2 | 9/2015 | Marnfeldt |
| 9,248,279 B2 | 2/2016 | Chen et al. |
| 9,259,574 B2 | 2/2016 | Aghassian et al. |
| 9,302,112 B2 | 4/2016 | Bornzin et al. |
| 9,381,356 B2 | 7/2016 | Parker et al. |
| 9,387,334 B2 | 7/2016 | Lee et al. |
| 9,656,090 B2 | 5/2017 | Goetz |
| 9,662,495 B2 | 5/2017 | Moffitt et al. |
| 2012/0095529 A1 | 4/2012 | Parramon et al. |
| 2012/0239115 A1* | 9/2012 | Lee ............... A61N 1/37247 607/59 |
| 2014/0296737 A1* | 10/2014 | Parker ............. A61B 5/04001 600/554 |
| 2014/0343623 A1 | 11/2014 | Alves et al. |
| 2015/0012061 A1 | 1/2015 | Chen |
| 2015/0080982 A1 | 3/2015 | Funderburk |
| 2015/0231402 A1 | 8/2015 | Aghassian |
| 2015/0360038 A1 | 12/2015 | Zottola et al. |
| 2016/0144183 A1 | 5/2016 | Marnfeldt |
| 2016/0157769 A1 | 6/2016 | Min et al. |
| 2017/0189689 A1 | 7/2017 | Steinke et al. |
| 2017/0281958 A1 | 10/2017 | Serrano Carmona et al. |
| 2017/0281959 A1 | 10/2017 | Serrano Carmona et al. |
| 2017/0296823 A1 | 10/2017 | Hershey et al. |
| 2018/0056068 A1 | 3/2018 | Zhang et al. |
| 2018/0056078 A1 | 3/2018 | Kashyap et al. |
| 2018/0071513 A1 | 3/2018 | Weiss et al. |
| 2018/0071520 A1 | 3/2018 | Weerakoon et al. |
| 2018/0214701 A1 | 8/2018 | Zhang et al. |
| 2021/0052889 A1* | 2/2021 | Grahn ............... A61N 1/36157 |

FOREIGN PATENT DOCUMENTS

| | | |
|---|---|---|
| WO | 2012/155185 A1 | 11/2012 |
| WO | 2017/176474 A1 | 10/2017 |

OTHER PUBLICATIONS

I. Akhoun et al., "Electrically evoked compound action potential artifact rejection by independent component analysis: Technique validation," Hearing Research 302, pp. 60-73 (2013).

M. Hughes, "Fundamentals of Clinical ECAP Measures in Cochlear Implants: Part 1: Use of the ECAP in Speech Processor Programming (2nd Ed.)," Audiology Online (Nov. 8, 2010) (http:// www.audiologyonline.com/articles/fundamentalsclinicalecapmeasuresin846).

H. Mino & J. Rubenstein, "Effects of Neural Refractoriness on Spatio-Temporal Variability in Spike Initiations with Eletrical Stimulation," IEEE Trans. on Neural Sys. & Rehabilitation Eng., vol. 14, No. 3, pp. 273-280 (2006).

M. Moffit et al., A Novel 3-Dimensional Algorithm for Model-Based Programming in Spinal Cord Stimuation (SCS): Illumina-3D™, presentation (2013).

J. Paz, "Physiological Midline Mapping Based on Spinal Cord Stimulation (SCS) Response Using the 32-Contact Paddle Lead," 19$^{th}$ NANS Annual Meeting (Dec. 13-15, 2015).

Precision Spectra™ System Programming Manual, Boston Scientific Corp., 90834018-18 Rev A (2016).E. Viezi et al., "Spinal Cord Stimulation (SCS) with Anatomically Guided (3D) Neural Targeting Shows Superior Chronic Axial Low Back Pain Relief Compared to Traditional SCS—LUMINA Study," Pain Medicine, pp. 1-15 (2017).

J. Rubinstein et al., "Pseudospontaneous activity: stochastic independence of auditory nerve fibers with electrical stimulation," Hear Res., 127(1-2), pp. 108-118 (1999) (abstract only).

J.L. Shils et al., "Intraoperative Neurophysiologic Methods for Spinal Cord Stimulator Placement Under General Anesthesia," Neuromodulation: Technology at the Neural Interface, vol. 15(6), pp. 560-572 (2012).

A. Taghva et al., "Intraoperative Electromyography as an Adjunct to Sacral Neuromodulation for Chronic Pelvic Pain," Neuromodulation: Technology at the Neural Interface, vol. 18(1), pp. 62-66 (2015).

E. Viezi et al., "Spinal Cord Stimulation (SCS) with Anatomically Guided (3D) Neural Targeting Shows Superior Chronic Axial Low Back Pain Relief Compared to Traditional SCS—Lumina Study," Pain Medicine, pp. 1-15 (2017).

Extended European Search Report regarding corresponding EP Application No. 19159974.5, dated Aug. 7, 2019.

* cited by examiner

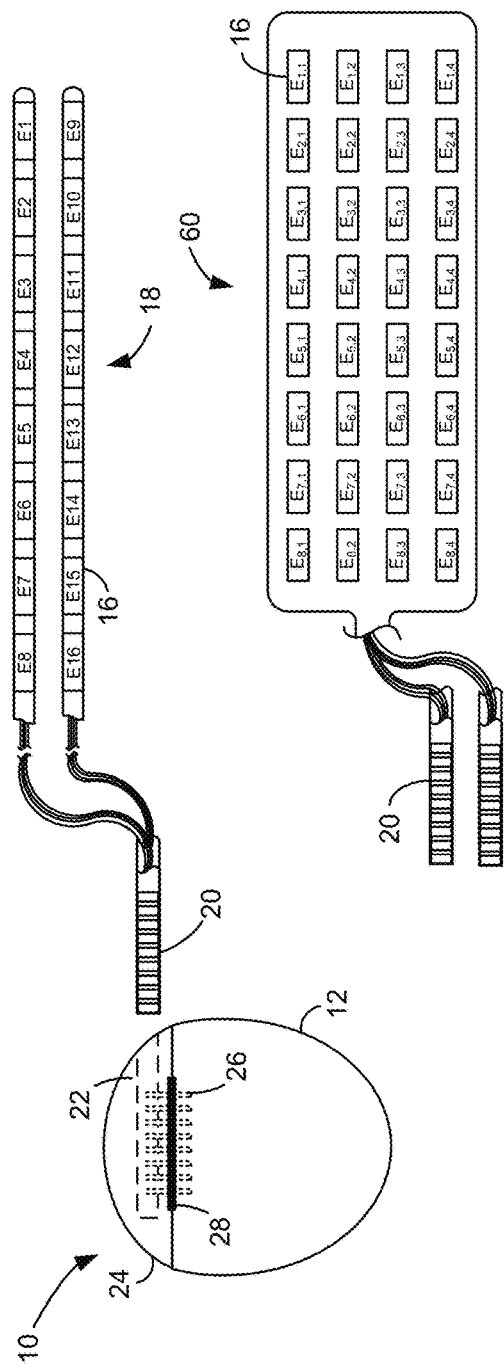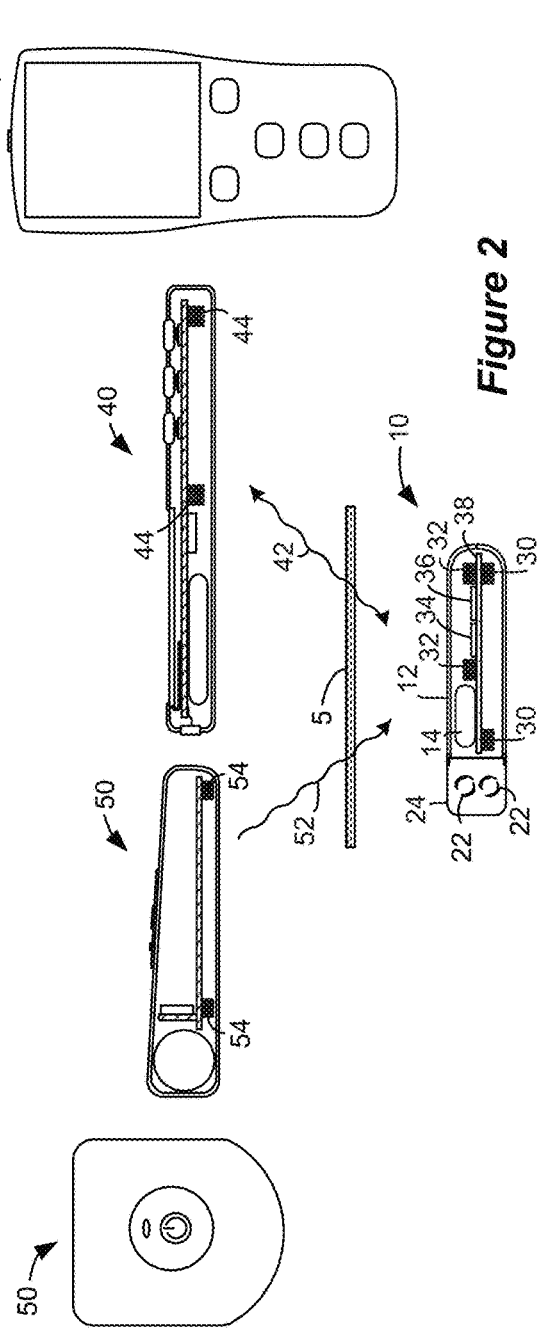
Figure 1
Figure 2

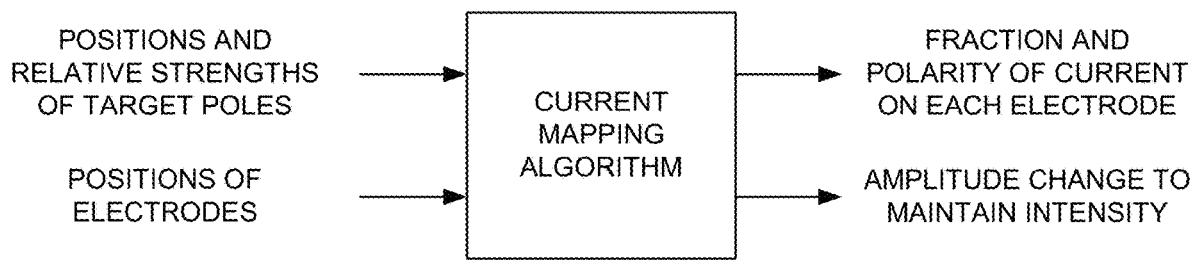
*Figure 5*
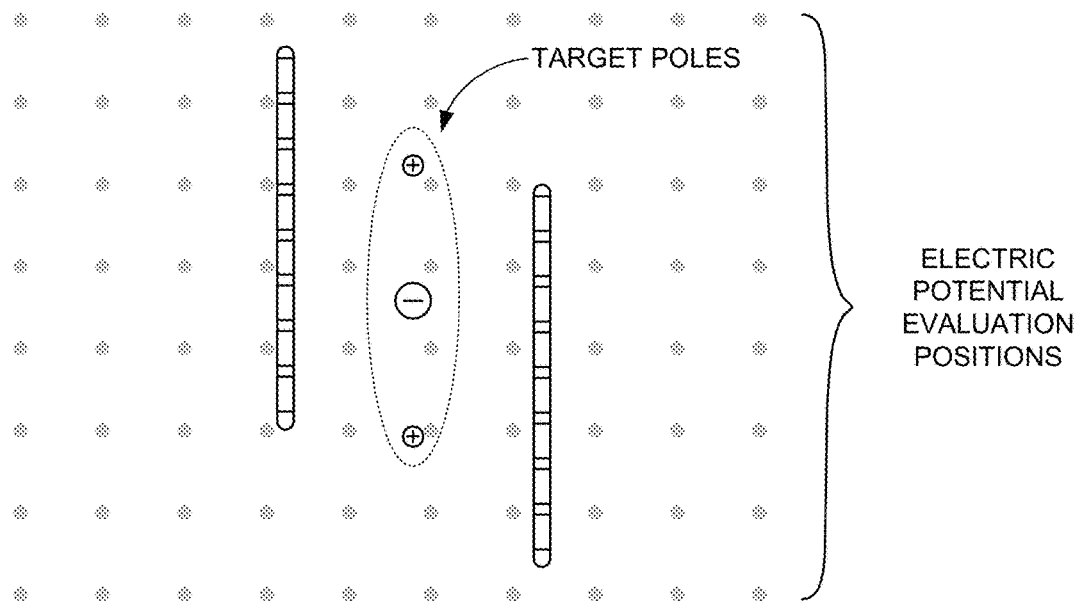
*Figure 6*
$$\begin{bmatrix} V_1 \\ \vdots \\ V_m \end{bmatrix}$$
φ
*Figure 7A*
$$\begin{bmatrix} V_{1,1} & \cdots & V_{1,n} \\ \vdots & \ddots & \vdots \\ V_{m,1} & \cdots & V_{m,n} \end{bmatrix}$$
A
*Figure 7B*
$$\begin{bmatrix} x_1 \\ \vdots \\ x_n \end{bmatrix}$$
j
*Figure 7C*

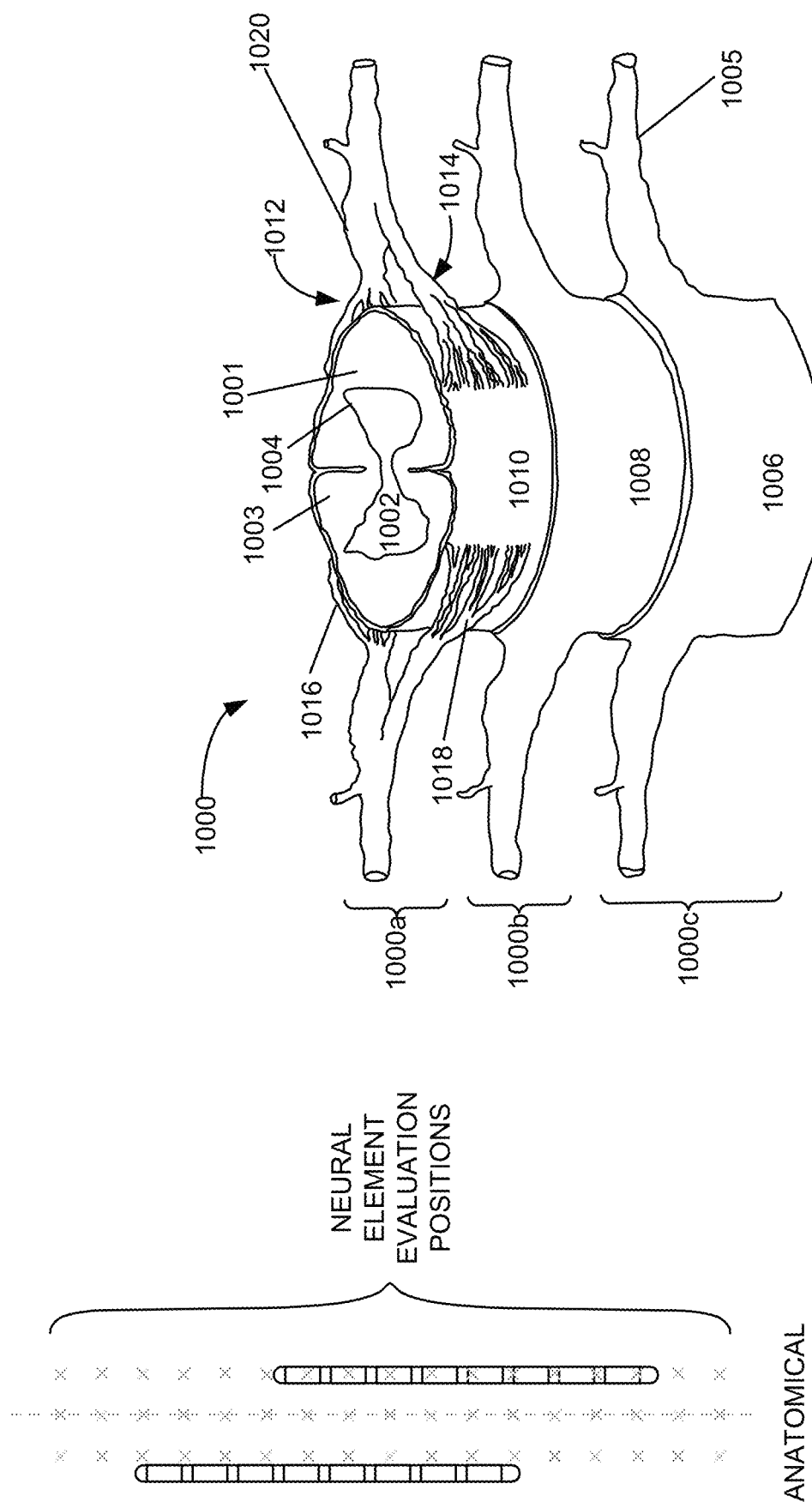

VIRTUAL TARGET POLE ADJUSTMENT BASED ON NERVE ROOT TRAJECTORY

CROSS REFERENCE TO RELATED APPLICATIONS

This is a non-provisional application of U.S. Provisional Patent Application Ser. No. 62/638,786, filed Mar. 5, 2018, which is incorporated by reference, and to which priority is claimed.

FIELD OF THE TECHNOLOGY

Implantable stimulation devices deliver electrical stimuli to nerves and tissues for the therapy of various biological disorders. The present application is related to a technique to improve the treatment of chronic pain using a Spinal Cord Stimulation (SCS) system. More specifically, the present application relates to techniques to adjust target stimulation poles based on nerve root trajectory.

INTRODUCTION

As shown in FIG. 1, a traditional SCS system includes an implantable neurostimulator such as an Implantable Pulse Generator (IPG) 10, which includes a device case 12 that is formed from a biocompatible material such as titanium. The case 12 typically holds the circuitry and battery 14 (FIG. 2) necessary for the IPG 10 to function, which battery 14 may be either rechargeable or primary in nature. The IPG 10 delivers electrical stimulation to a patient's nerves and tissues through electrodes 16, which, in a SCS system are typically implantable within the epidural space within the spinal column. Common electrode arrangements include a linear arrangement along a percutaneous lead 18 and a two-dimensional arrangement on a paddle lead 60. The proximal ends of the leads 18 and 60 include lead connectors 20 that are connectable to the IPG 10 at one or more connector blocks 22 fixed in a header 24, which can comprise an epoxy, for example. Contacts in the connector blocks 22 make contact with electrode terminals in the lead connectors 20, and communicate with the circuitry inside the case 12 via feedthrough pins 26 passing through a hermetic feedthrough 28 to allow such circuitry to provide stimulation to or monitor the various electrodes 16. The number and arrangement of electrodes 16 on a percutaneous lead 18 or a paddle lead 60 can vary. When percutaneous leads 18 are employed, it is common for multiple such leads 18 to be implanted at different anatomical locations along the spinal canal.

As shown in FIG. 2, IPG 10 contains a charging coil 30 for wireless charging of the IPG's battery 14 using an external charger 50, assuming that battery 14 is a rechargeable battery. If IPG 10 has a non-rechargeable (primary) battery 14, charging coil 30 in the IPG 10 and the external charger 50 can be eliminated. IPG 10 also contains a telemetry coil antenna 32 for wirelessly communicating data with an external controller device 40, which is explained further below. In other examples, antenna 32 can comprise a short-range RF antenna such as a slot, patch, or wire antenna. IPG 10 also contains control circuitry such as a microcontroller 34, and one or more Application Specific Integrated Circuit (ASICs) 36, which can be as described for example in U.S. Pat. No. 8,768,453. ASIC(s) 36 can include stimulation circuitry for providing stimulation pulses at one or more of the electrodes 16 and may also include telemetry modulation and demodulation circuitry for enabling bidirectional wireless communications at antenna 32, battery charging and protection circuitry coupleable to charging coil 30, DC-blocking capacitors in each of the current paths proceeding to the electrodes 16, etc. Components within the case 12 are integrated via a printed circuit board (PCB) 38.

FIG. 2 further shows the external devices referenced above, which may be used to communicate with the IPG 10, in plan and cross section views. External controller (or, remote controller) 40 may be used to control and monitor the IPG 10 via a bidirectional wireless communication link 42 that passes through a patient's tissue 5. For example, the external controller 40 may be used to provide or adjust a stimulation program for the IPG 10 to execute that provides stimulation to the patient. The stimulation program includes a number of stimulation parameters, such as which electrodes are selected for stimulation; whether such active electrodes are to act as anodes or cathodes; and the amplitude (e.g., current), frequency, and duration of stimulation at the active electrodes, assuming such stimulation comprises stimulation pulses as is typical.

Communication on link 42 can occur via magnetic inductive coupling between a coil antenna 44 in the external controller 40 and the IPG 10's telemetry coil 32 as is well known. Typically, the magnetic field comprising link 42 is modulated, for example via Frequency Shift Keying (FSK) or the like, to encode transmitted data. For example, data telemetry via FSK can occur around a center frequency of fc=125 kHz, with a 129 kHz signal representing transmission of a logic '1' bit and a 121 kHz signal representing a logic '0' bit. However, transcutaneous communications on link 42 need not be by magnetic induction, and may comprise short-range RF telemetry (e.g., Bluetooth, WiFi, Zigbee, MICS, etc.) if antennas 44 and 32 and their associated communication circuitry are so configured. The external controller 40 is generally similar to a cell phone and includes a hand-holdable, portable housing.

External charger 50 provides power to recharge the IPG's battery 14 should that battery be rechargeable. Such power transfer occurs by energizing a charging coil 54 in the external charger 50, which produces a magnetic field comprising transcutaneous link 52, which may occur with a different frequency ($f_2$=80 kHz) than data communications on link 42. This magnetic field 52 energizes the charging coil 30 in the IPG 10, and the induced voltage is rectified, filtered, and used to recharge the battery 14. Link 52, like link 42, can be bidirectional to allow the IPG 10 to report status information back to the external charger 50, such as by using Load Shift Keying as is well-known. For example, once circuitry in the IPG 10 detects that the battery 14 is fully charged, it can cause charging coil 30 to signal that fact back to the external charger 50 so that charging can cease. Like the external controller 40, external charger 50 generally comprises a hand-holdable and portable housing.

External controller 40 and external charger 50 are described in further detail in U.S. Patent Application Publication 2015/0080982. Note also that the external controller 40 and external charger 50 can be partially or fully integrated into a single external system, such as disclosed in U.S. Pat. Nos. 8,335,569 and 8,498,716.

SUMMARY

A system is disclosed comprising a neurostimulator that is connectable to a plurality of electrodes that are implantable in a patient; and an external device that is configured to determine a trajectory of each of one or more dorsal roots of the patient; receive one or more inputs that are associated with a desired location of a stimulation field that is to be generated by the neurostimulator; determine an electrode configuration that causes the stimulation field to be substantially parallel with the trajectory of the dorsal root that is nearest to the desired location of the stimulation field; and communicate the electrode configuration to the neurostimulator.

The system may be configured to determine the trajectory of each of the one or more dorsal roots of the patient by: after the neurostimulator provides stimulation at each of a plurality of sample stimulation locations, determining a measurement of a neural response to the stimulation at each of the plurality of sample stimulation locations; and determining the trajectory of each of the one or more dorsal roots based on the measured neural response to the stimulation at each of the plurality of sample stimulation locations. The neural response to the stimulation at each of the plurality of sample stimulation locations may be measured based on one or more properties of an evoked compound action potential (ECAP) at one or more of the plurality of electrodes. The one or more properties of the ECAP may include a magnitude and a shape of the ECAP. The magnitude and the shape of the ECAP may be utilized to calculate a neural response metric that is indicative of a degree of desirable stimulation. The external device may be configured to generate a neural response map that includes a metric of the measured neural response at each of the plurality of sample stimulation locations. The external device may be configured to display the neural response map. Determining the trajectory of each of the one or more dorsal roots based on the neural response to stimulation at the plurality of sample stimulation locations may include performing a mathematical operation on the metric over the neural response map.

The system may be configured to determine the trajectory of each of the one or more dorsal roots of the patient by: after the neurostimulator provides stimulation at each of a plurality of sample stimulation locations, determining a stimulation amplitude at which the patient perceives the stimulation at each of the plurality of sample stimulation locations; and determining the trajectory of each of the one or more dorsal roots based on the stimulation amplitude at which the patient perceives the stimulation at each of the plurality of sample stimulation locations. The neurostimulator may provide stimulation at each of the plurality of sample stimulation locations at increasing stimulation amplitudes until the patient perceives the stimulation. The external device may be configured to generate a patient response map based on the stimulation amplitude at which the patient perceives the stimulation at each of the plurality of sample stimulation locations. The external device may be configured to display the patient response map. Determining the trajectory of each of the one or more dorsal roots based on the stimulation amplitude at which the patient perceives the stimulation at each of the plurality of sample stimulation locations may include performing a mathematical operation on the stimulation amplitude over the patient response map.

The one or more inputs may include a center point of the stimulation field and/or a focus of the stimulation field.

The external device may be configured to determine an electrode configuration that causes the stimulation field to be substantially parallel with the trajectory of the dorsal root that is nearest to the desired location of the stimulation field by determining a location of one or more target poles based on the one or more inputs, wherein the target poles are aligned with or symmetrical about a path that is substantially parallel with the trajectory of the dorsal root that is nearest to the desired location of the stimulation field; estimating an electric field that would result from stimulation at the one or more target poles; and determining the electrode configuration that corresponds to the estimated electric field. The one or more target poles may include a target cathode at a center point of the stimulation field and two equal target anodes that are each positioned at an equal distance from the center point of stimulation along the path. The electrode configuration may specify a polarity and magnitude of stimulation for the plurality of electrodes. The external device may be a clinician's programmer or a remote controller.

The external device may be further configured to determine an electric field that would result from stimulation using the electrode configuration; determine a response of neural elements to the electric field at a plurality of neural element evaluation positions, wherein the neural element evaluation positions include positions that are substantially parallel with the trajectory of each of the one or more dorsal roots; and adjust the electrode configuration if the determined response of neural elements deviates from a desired response. The external device may be further configured to estimate a location of one or more dorsal root ganglia based, at least in part, on the trajectory of each of one or more dorsal roots of the patient, and the neural element evaluation positions may include soma neural element evaluation positions that are located proximate to the estimated location of the one or more dorsal root ganglia. The external device may be configured to adjust the electrode configuration by adjusting an amplitude of stimulation that is provided at the plurality of electrodes.

An external device is disclosed that is configured to communicate with a neurostimulator and that is configured to determine a trajectory of each of one or more dorsal roots of a patient; receive one or more inputs that are associated with a desired location of a stimulation field that is to be generated by the neurostimulator; determine an electrode configuration that causes the stimulation field to be substantially parallel with the trajectory of the dorsal root that is nearest to the desired location of the stimulation field; and communicate the electrode configuration to the neurostimulator.

The external device may be configured to determine the trajectory of each of the one or more dorsal roots of the patient by: after the neurostimulator provides stimulation at each of a plurality of sample stimulation locations, determining a measurement of a neural response to the stimulation at each of the plurality of sample stimulation locations; and determining the trajectory of each of the one or more dorsal roots based on the measured neural response to the stimulation at each of the plurality of sample stimulation locations. The neural response to the stimulation at each of the plurality of sample stimulation locations may be measured based on one or more properties of an evoked compound action potential (ECAP) at one or more of a plurality of electrodes that are connectable to the neurostimulator. The external device may be configured to generate a neural response map that comprises a metric of the measured neural response at each of the plurality of sample stimulation locations. The external device may be configured to display the neural response map. Determining the trajectory of each of the one or more dorsal roots based on the neural response to stimulation at the plurality of sample stimulation locations may include performing a mathematical operation on the metric over the neural response map.

The external device may be configured to determine the trajectory of each of the one or more dorsal roots of the patient by: after the neurostimulator provides stimulation at each of a plurality of sample stimulation locations, determining a stimulation amplitude at which the patient perceives the stimulation at each of the plurality of sample stimulation locations; and determining the trajectory of each of the one or more dorsal roots based on the stimulation amplitude at which the patient perceives the stimulation at each of the plurality of sample stimulation locations. The neurostimulator may provide stimulation at each of a plurality of sample stimulation locations at increasing stimulation amplitudes until the patient perceives the stimulation. The external device may be configured to generate a patient response map based on the stimulation amplitude at which the patient perceives the stimulation at each of the plurality of sample stimulation locations. The external device may be configured to display the patient response map. Determining the trajectory of each of the one or more dorsal roots based on the stimulation amplitude at which the patient perceives the stimulation at each of the plurality of sample stimulation locations may include performing a mathematical operation on the stimulation amplitude over the patient response map.

The one or more inputs may include a center point of the stimulation field and/or a focus of the stimulation field.

The external device may be configured to determine an electrode configuration that causes the stimulation field to be substantially parallel with the trajectory of the dorsal root that is nearest to the desired location of the stimulation field by determining a location of one or more target poles based on the one or more inputs, wherein the target poles are aligned with or symmetrical about a path that is substantially parallel with the trajectory of the dorsal root that is nearest to the desired location of the stimulation field; estimating an electric field that would result from stimulation at the one or more target poles; an determining the electrode configuration that corresponds to the estimated electric field. The one or more target poles may include a target cathode at a center point of the stimulation field and two equal target anodes that are each positioned at an equal distance from the center point of stimulation along the path. The electrode configuration may specify a polarity and magnitude of stimulation for the plurality of electrodes. The external device may be a clinician's programmer or a remote controller.

The external device may be further configured to determine an electric field that would result from stimulation using the electrode configuration; determine a response of neural elements to the electric field at a plurality of neural element evaluation positions, wherein the neural element evaluation positions include positions that are substantially parallel with the trajectory of each of the one or more dorsal roots; and adjust the electrode configuration if the determined response of neural elements deviates from a desired response. The external device may be further configured to estimate a location of one or more dorsal root ganglia based, at least in part, on the trajectory of each of one or more dorsal roots of the patient, and the neural element evaluation positions may include soma neural element evaluation positions that are located proximate to the estimated location of the one or more dorsal root ganglia. The external device may be configured to adjust the electrode configuration by adjusting an amplitude of stimulation that is provided at the plurality of electrodes.

A non-transitory computer-readable medium is disclosed comprising instructions configured to cause control circuitry to determine a trajectory of each of one or more dorsal roots of a patient; receive one or more inputs that are associated with a desired location of a stimulation field that is to be generated by a neurostimulator; determine an electrode configuration that causes the stimulation field to be substantially parallel with the trajectory of the dorsal root that is nearest to the desired location of the stimulation field; and communicate the electrode configuration to the neurostimulator.

A method is disclosed comprising determining a trajectory of each of one or more dorsal roots of a patient; receiving one or more inputs that are associated with a desired location of a stimulation field that is to be generated by a neurostimulator; determining an electrode configuration that causes the stimulation field to be substantially parallel with the trajectory of the dorsal root that is nearest to the desired location of the stimulation field; and communicating the electrode configuration to the neurostimulator.

BRIEF DESCRIPTION OF THE DRAWINGS

FIG. 1 shows an implantable pulse generator (IPG).

FIG. 2 shows a cross section of the IPG of FIG. 1 as implanted in a patient, as well as external devices that support the IPG, including an external charger and external controller.

FIG. 5 is a block diagram that shows the inputs to and the outputs from a current mapping algorithm that can be used to determine the parameters of spinal cord stimulation in accordance with an example of the disclosure.

FIG. 6 illustrates a portion of the current mapping algorithm that is used to determine the fraction and polarity of electrodes that best matches a target stimulation field in accordance with an example of the disclosure.

FIGS. 7A-7C show the properties of different matrices that are used in the current mapping algorithm in accordance with an example of the disclosure.

FIG. 9 illustrates a portion of the current mapping algorithm that is used to maintain an intensity of stimulation in accordance with an example of the disclosure.

FIG. 10 shows a portion of a spinal cord and illustrates anatomical features that are relevant to aspects of the disclosure.

DETAILED DESCRIPTION

As mentioned above, the electrical stimulation that the IPG 10 is capable of delivering is highly customizable with respect to selected electrodes, electrode current amplitude and polarity, pulse duration, pulse frequency, etc. Due to uncertainties in the location of electrodes with respect to neural targets, the physiological response of a patient to stimulation patterns, and the nature of the electrical environment within which the electrodes are positioned, it is essentially impossible to determine the stimulation parameters that might provide effective stimulation therapy for a particular patient prior to implementing stimulation therapy. Thus, in order to determine whether the IPG 10 is capable of delivering effective therapy, and, if so, the stimulation parameters that define such effective therapy, the patient's response to different stimulation parameters is typically evaluated during a trial stimulation phase prior to the permanent implantation of the IPG 10.

Figure 3:
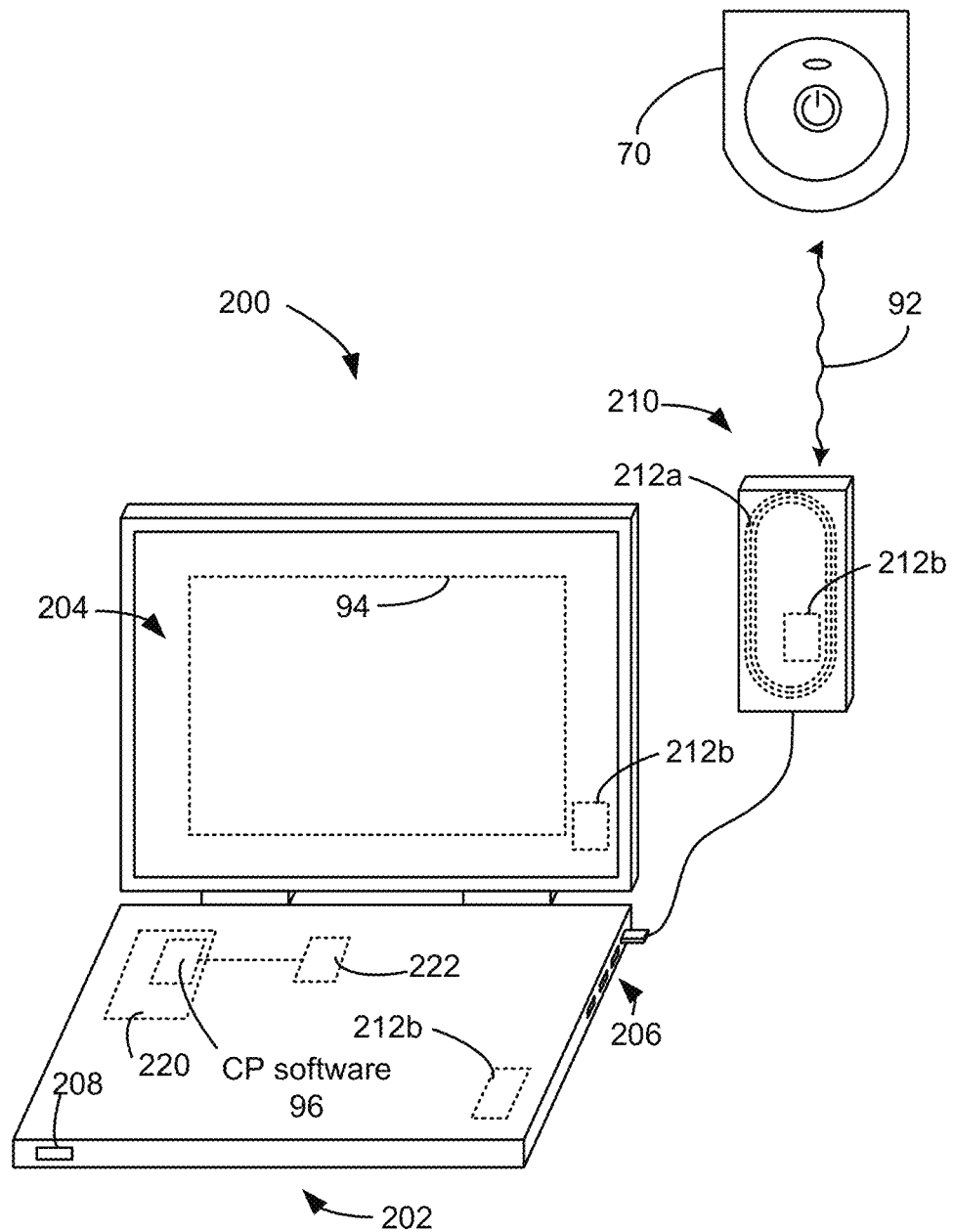
FIG. 3 shows components of a clinician's programmer system, including components for communicating with an external trial stimulator in accordance with an example of the disclosure.

During the trial stimulation phase, the distal ends of the lead(s) are implanted within the epidural space along the spinal cord while the proximal ends of the lead(s), including the electrode terminals 20, are ultimately coupled to an external neurostimulator such as external trial stimulator (ETS) 70, which is not implanted in the patient. The ETS 70, which is shown in FIG. 3, essentially mimics operation of the IPG 10 to provide stimulation to the implanted electrodes 16. This allows the effectiveness of stimulation therapy, such as whether therapy has alleviated the patient's symptoms, to be verified. Trial stimulation using the ETS 70 further allows for the determination of a particular stimulation program that seems promising for the patient to use once the IPG 10 is later implanted into the patient.

The stimulation program executed by the ETS 70 can be provided or adjusted via a wired or wireless link (wireless link 92 shown) from an additional external device known as a clinician's programmer 200, which includes features (described below) that enable a clinician to hone in on the appropriate stimulation therapy settings. As shown, CP system 200 can comprise a computing device 202, such as a desktop, laptop, or notebook computer, a tablet, a mobile smart phone, a Personal Data Assistant (PDA)-type mobile computing device, etc. (hereinafter "CP computer"). In FIG. 3, CP computer 202 is shown as a laptop computer that includes typical computer user interface means such as a screen 204, a mouse, a keyboard, speakers, a stylus, a printer, etc., not all of which are shown for convenience. Also shown in FIG. 3 is a communication head 210, which is coupleable to a suitable port on the CP computer 202, such as a USB port 206, for example. While the CP system is shown in communication with the ETS 70, the CP system 200 is also configured to communicate with the IPG 10 once it is implanted.

Communication between the CP system 200 and the ETS 70 or IPG 10 may comprise magnetic inductive or short-range RF telemetry schemes as already described, and in this regard the ETS 70 and the CP computer 202 and/or the communication head 210 (which can be placed proximate to the IPG 10 or ETS 70) may include antennas compliant with the telemetry means chosen. For example, the communication head 210 can include a coil antenna 212a, a short-range RF antenna 212b, or both. The CP computer 202 may also communicate directly with the IPG 10 of the ETS 70, for example using an integral short-range RF antenna 212b.

If the CP system 200 includes a short-range RF antenna (either in CP computer 202 or communication head 210), such antenna can also be used to establish communication between the CP system 200 and other devices, and ultimately to larger communication networks such as the Internet. The CP system 200 can typically also communicate with such other networks via a wired link provided at an Ethernet or network port 208 on the CP computer 202, or with other devices or networks using other wired connections (e.g., at USB ports 206).

To program stimulation parameters, the clinician interfaces with a clinician's programmer graphical user interface (CP GUI) 94 provided on the display 204 of the CP computer 202. As one skilled in the art understands, the CP GUI 94 can be rendered by execution of CP software 96 on the CP computer 202, which software may be stored in the CP computer's non-volatile memory 220. Such non-volatile memory 220 may include one or more non-transitory computer-readable storage mediums including, for example, magnetic disks (fixed, floppy, and removable) and tape, optical media such as CD-ROMs and digital video disks (DVDs), and semiconductor memory devices such as Electrically Programmable Read-Only Memory (EPROM), Electrically Erasable Programmable Read-Only Memory (EEPROM), and USB or thumb drive. One skilled in the art will additionally recognize that execution of the CP software 96 in the CP computer 202 can be facilitated by control circuitry 222 such as a microprocessor, microcomputer, an FPGA, other digital logic structures, etc., which is capable of executing programs in a computing device. Such control circuitry 222 when executing the CP software 96 will in addition to rendering the CP GUI 94 enable communications with the ETS 70 through a suitable antenna 212a or 212b, either in the communication head 210 or the CP computer 202 as explained earlier, so that the clinician can use the CP GUI 94 to communicate the stimulation parameters to the ETS 70.

Figure 4:
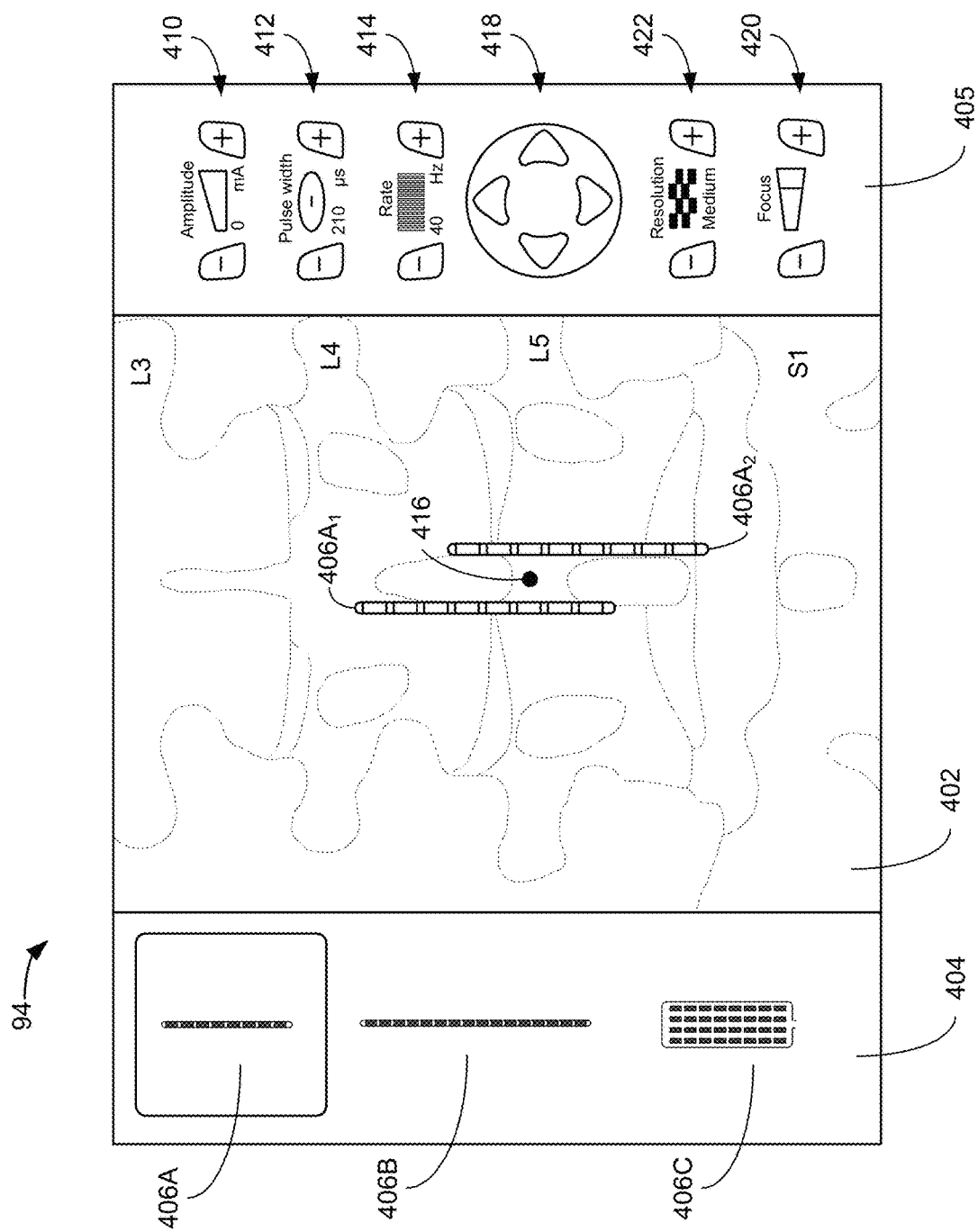
FIG. 4 shows an example of a graphical user interface that can be provided on the clinician's programmer system in accordance with an example of the disclosure.

An example of a portion of the CP GUI 94 is shown in FIG. 4. The illustrated portion of the GUI 94 includes fluoroscopic image 402, which shows the implanted leads relative to anatomical structures, such as vertebrae. Using the illustrated interface, a user can select a representation 406 of the implanted electrode lead from the lead interface 404, which includes representations 406 of various types of lead products such as 1×8 percutaneous lead representation 406A, 1×16 percutaneous lead representation 406B, and 4×8 paddle lead representation 406C. The user can then drag the selected lead representation 406 onto the fluoroscopic image 402 and manipulate its size and orientation until it aligns with the implanted electrode lead in the image 402. Because the representations 406 are programmed with properties of the lead such as electrode size, shape, and spacing, the positioning of a lead representation 406 over its corresponding implanted lead in the fluoroscopic image 402 relates the locations of the electrodes to the image 402. This enables a user to subsequently visualize through the GUI 94 the anatomical location of electrical stimulation as described below. Relative electrode locations can also be determined absent an image through measurements of inter-electrode impedance and voltages induced at electrodes by stimulation at other electrodes.

Such anatomical visualization of electrical stimulation can be beneficial in determining the desired stimulation program due to the spatial relationship between the point of stimulation and the location at which the effect of stimulation is perceived by a patient. While the precise mechanism by which spinal cord stimulation interrupts the sensation of pain is not fully understood, it is understood that the stimulation of a spinal nerve on a particular side of a patient's body results in the perception of stimulation (or simply the interruption of what was previously perceived as pain) on the same side of the body. For example, pain in the upper right leg, which is perceived as a result of the transmission of a neurological signal through sensory neurons from the location of the pain through a spinal nerve on the same side of the body and into the spinal cord where it is further transmitted to the brain, is interrupted by the application of electrical stimulation to the spinal nerve through which the pain signal travels (i.e., the spinal nerve on the right side of the body). Therefore, the visualization of the anatomical point of stimulation provides information that can guide the user in determining the appropriate stimulation parameters to treat a patient's particular pain symptoms.

Various inputs regarding the location and properties of stimulation can be provided by the user through interactive elements in the stimulation interface 405 of the GUI 94 as further illustrated in FIG. 4. The stimulation amplitude, pulse width, and frequency can be adjusted using the buttons 410, 412, and 414, respectively. The center point 416 of the desired stimulation field can be moved horizontally and vertically using the arrows 418. The shape of the target stimulation field can be customized, but, in one example, the target stimulation field may be represented by a tripole consisting of a target cathode at the center point of stimulation and two target anodes at equal distances from the cathode along a line that is parallel with the anatomical midline (i.e. along a vertical line in the interface 94). The focus of the target stimulation field, which is the distance between the target cathode and each target anode, can be adjusted using the focus buttons 420. The magnitude of the adjustments that are effected via the arrows 418 and the focus buttons 420 can be set at different granularity levels (e.g., coarse, medium, and fine) via the resolution buttons 422.

While the target stimulation field could be generated by providing stimulation at the locations of the target poles (i.e., the target cathode and target anodes), the target poles do not necessarily correspond to the location of physical electrodes. Thus, a current mapping algorithm, which is part of the CP software 96, is employed to compute the fraction of the total stimulation current that should be sourced to or sunk from each physical electrode to best represent the electric field that would result from stimulation at the target poles. As illustrated in FIG. 5, the inputs to the current mapping algorithm are the positions and relative strengths of the target poles and the positions of the physical electrodes. From these inputs, the current mapping algorithm outputs the current fraction and polarity of current that should be delivered to each physical electrode (i.e., the electrode allocation) to mimic the target stimulation field as well as an amplitude change that is necessary to maintain stimulation intensity as is now briefly explained. These properties form part of the electrode configuration that is communicated to the neurostimulator.

The current mapping algorithm includes a model (such as a finite element model) that can be used to evaluate properties of the electric field that would be generated as a result of stimulation at the target poles. As used herein, modeling an electric field or generating a model of an electric field refers to determining one or more electrical properties at different spatial locations. Similarly, an electric field model refers to the values of the one or more electrical properties at the different spatial locations. The electrical properties may include the magnitude and/or direction of the electric field itself, the magnitude of an electric potential, the magnitude of a current, or other electrical properties at the different spatial locations. Thus, an electric field model does not necessarily refer to values of the strength and direction of an electric field (as the model may include a collection of other electrical values such as electric potentials) and does not imply that values exist at every spatial location within a volume of tissue but rather at a determined number of locations.

In an example, the model takes into account the electrical properties of different anatomical structures such as white matter, gray matter, cerebral spinal fluid, epidural space, dura, and vertebral bone in the area of the target poles to determine the electric potential that would be induced at each of m electric potential evaluation positions as a result of stimulation at the target poles. The electric potential evaluation positions may be arranged in a grid as shown in FIG. 6. While a small number of evaluation positions are shown for purposes of illustration, in an actual implementation the spatial resolution of the evaluation positions may be much higher. The modeled electric potentials at the m evaluation positions that would result from stimulation at the target poles form a m×1 vector, φ (FIG. 7A).

The model is also used to determine the electric potentials that would be induced at the in evaluation positions as a result of stimulation via n physical electrode arrangements. While the modeled electrode arrangements can include any combination of electrodes (e.g. bipoles, tripoles, etc.), in one example, the n electrode arrangements are each bipole arrangements (e.g., E1 is 100% cathode and E2 is 100% anode, E2 is 100% cathode and E3 is 100% anode, etc.). The electric potentials at the m evaluation positions that are determined as a result of modeling stimulation via the n electrode arrangements form a m×n transfer matrix, A (FIG. 7B). Any number of electrode arrangements can be modeled to increase the size of the transfer matrix A, and the solution accuracy and computational difficulty are both increased as the number of electrode arrangements n is increased.

The electric potentials that would be formed at the m evaluation positions as a result of a combination of various electrode arrangements can be determined by multiplying the transfer matrix A with a n×1 vector j (FIG. 7C) that specifies the proportions (X) of each of the n electrode arrangements. The combination of electrode arrangements that would induce electric potentials at the m evaluation positions that best match those generated as a result of stimulation at the target poles can be determined by solving for the value of j that minimizes the equation $|\varphi-Aj|^2$. The relative proportions of the electrode arrangements in the calculated value of j can be converted to the electrode current fractions and polarities that would result in an electric potential field that most closely mimics the target stimulation field.

Figure 8A:
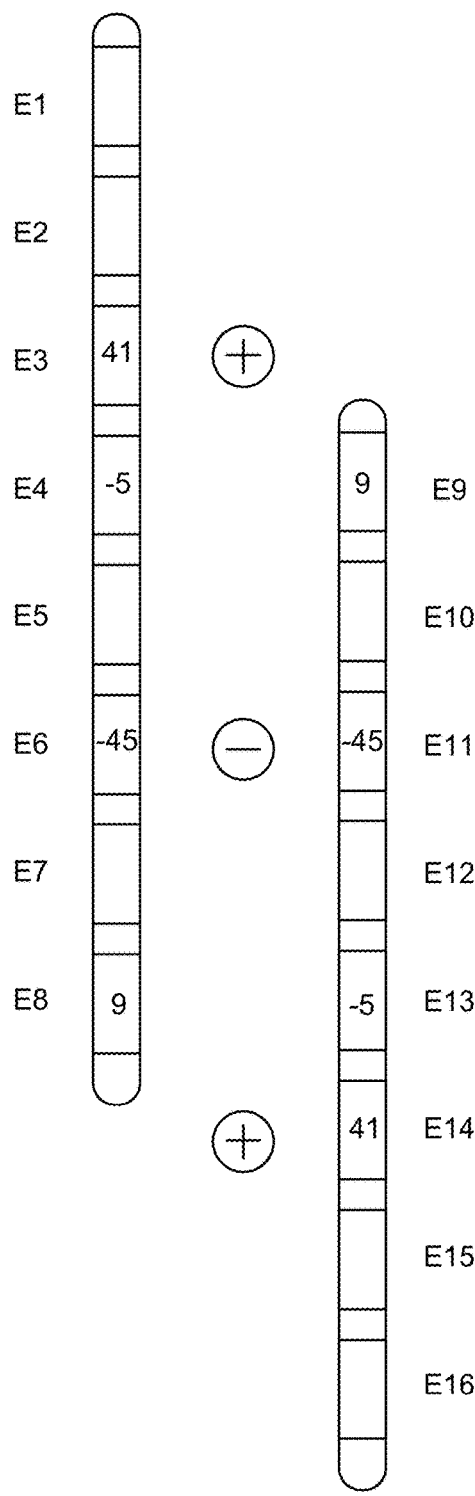
FIGS. 8A and 8B show examples of the determined allocation of current among electrodes for different target stimulation fields in accordance with an example of the disclosure.
Figure 8B:
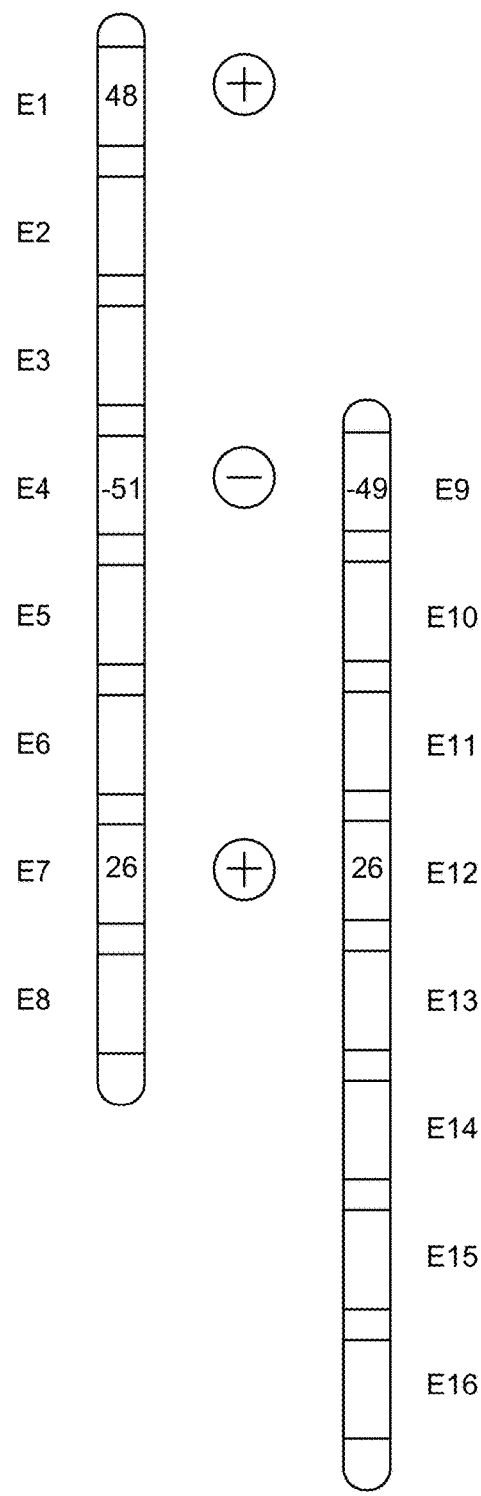
Figure 12:
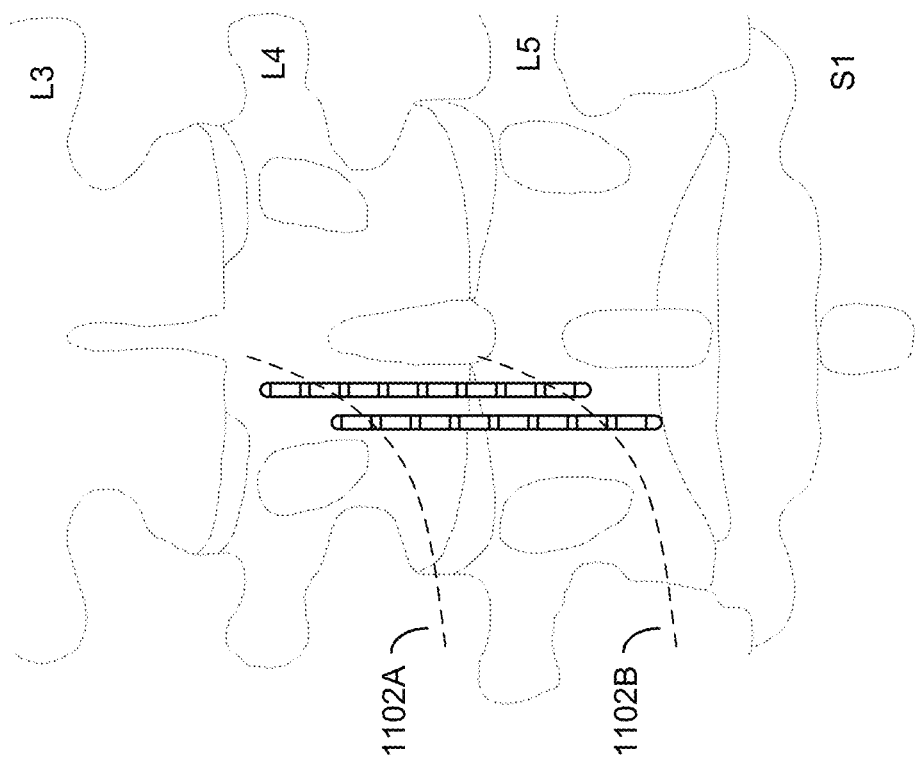
FIGS. 11 and 12 show lateral placements of three percutaneous leads and two percutaneous leads, respectively, in the spinal canal in accordance with an aspect of the disclosure.

The current fractions and polarities that may be computed by the current mapping algorithm for example target stimulation fields are illustrated in FIGS. 8A and 8B. In the figures, two percutaneous leads are shown. The leads are offset by three electrodes with the left lead inserted further than the right lead. In FIG. 8A, the target stimulation field is represented by a tripole having a center point of stimulation that is positioned between electrodes E6 and E11 and a focus of three times the electrode-to-electrode spacing on the leads. The output of the current mapping algorithm specifies that the target stimulation field is best represented when 41% of the anodic current is allocated to each of electrodes E3 and E14, 9% of the anodic current is allocated to each of electrodes E8 and E9, 45% of the cathodic current is allocated to each of electrodes E6 and E11, and 5% of the cathodic current is allocated to each of electrodes E4 and E13. In FIG. 8B, the target stimulation field is represented by the same tripole as in FIG. 8A except the center point of stimulation is shifted such that it is positioned between electrodes E4 and E9. The output of the current mapping algorithm specifies that this target stimulation field is best represented when 51% of the anodic current is allocated to electrode E4, 49% of the anodic current is allocated to electrode E9, 26% of the cathodic current is allocated to each of electrodes E7 and E12, and 48% of the cathodic current is allocated to electrode E1. The determination of current fractions and polarities that best match a target stimulation field is described in greater detail in U.S. Pat. No. 8,412,345, which is incorporated herein by reference in its entirety.

In addition to determining the fraction and polarity of current that should be delivered to each electrode to best represent the target stimulation field, the current mapping algorithm additionally determines whether and to what extent the total stimulation amplitude should be adjusted to maintain constant stimulation intensity. The determined allocation of current between the electrodes is input to the model described above to determine the resulting spatial distribution of electric potentials for a baseline stimulation amplitude (e.g., total stimulation amplitude of 1 mA). The modeled potentials are assumed to scale linearly with increasing stimulation amplitude and are adjusted from the baseline amplitude to the actual stimulation amplitude that is being used.

The current mapping algorithm then employs a neural element model to evaluate the response of neural elements to the electric field. The neural element model incorporates morphological and electrical properties to evaluate the response of neural elements to the different electric field properties that are observed at different neural element evaluation positions. For example, the neural element model may compute, based on the electric field properties, the transmembrane potentials that are induced at the Nodes of Ranvier of the dorsal column fibers. The evaluation positions are located along the assumed path of the dorsal column fibers along the anatomical midline as shown in FIG. 9. Note that the neural element evaluation positions are different from the electric potential evaluation positions shown in FIG. 6. Based on the modeled electric potentials as well as other stimulation parameters such as frequency and pulse width, the neural element model can be utilized to determine whether the neural elements at each evaluation position would be activated by the stimulation. Note that while the neural element evaluation positions are symmetrical with respect to the anatomical midline, they are not necessarily symmetrical with respect to the electrode leads and thus the allocation of current to different electrodes may result in the different activations of neural elements at different ones of the evaluation positions. For example, in FIG. 9, the right lead is positioned nearer to the assumed location of the dorsal column fibers (and therefore nearer to the evaluation positions), so stimulation using electrodes on the right lead would be expected to activate a larger number of dorsal column neural elements. Therefore, as the center point of stimulation is moved from left to right, the same stimulation amplitude would result in the activation of increasing numbers of neural elements. To maintain the same stimulation intensity as the location of stimulation is moved, the total stimulation amplitude is adjusted to keep the volume of activation (i.e., the number of neural elements that are determined to be activated by a particular electric field) relatively constant. U.S. Pat. No. 8,644,947, which is incorporated herein by reference in its entirety, describes in greater detail the adjustment of stimulation amplitude to maintain stimulation intensity.

FIG. 10 shows a portion of a spinal cord 1000. A typical transverse section of the spinal cord includes a "butterfly-shaped" central area of gray matter 1002 that is substantially surrounded by an ellipse-shaped outer area of white matter 1001. The white matter of the dorsal column 1003 includes mostly large myelinated axons that form afferent fibers that run in an axial direction. The dorsal portions of the "butterfly-shaped" central area of gray matter 1002 are referred to as dorsal horns 1004. In contrast to the dorsal column fibers that run in an axial direction, dorsal horn fibers can be oriented in many directions, including laterally with respect to the longitudinal axis of the spinal cord.

The spinal cord 1000 is enclosed within three layers of tissue, collectively called the meninges. SCS leads are typically implanted on or adjacent the outer layer of the meninges, called the dura mater 1006, which is shown in spinal cord segment 1000c. The dura mater has been removed in spinal cord segment 1000b to reveal the middle meninges, called the arachnoid 1008. The innermost meninges, the pia mater 1010, is shown in spinal cord segment 1000a.

Upon removal of the outer meningeal layers, it is seen that spinal nerves 1005 split into a dorsal root 1012 and a ventral root 1014, each of which comprises subdivisions referred to as rootlets. The dorsal rootlets are labeled 1016 and the ventral rootlets are labeled 1018. The dorsal root 1012 also includes a structure called the dorsal root ganglion 1020, which comprises cell bodies of the afferent neurons. The dorsal root 1012 contains afferent neurons, which carry sensory signals into the spinal cord, and the ventral root 1014 functions as an efferent motor root. The dorsal and ventral roots join to form mixed spinal nerves 1005.

Figure 11:
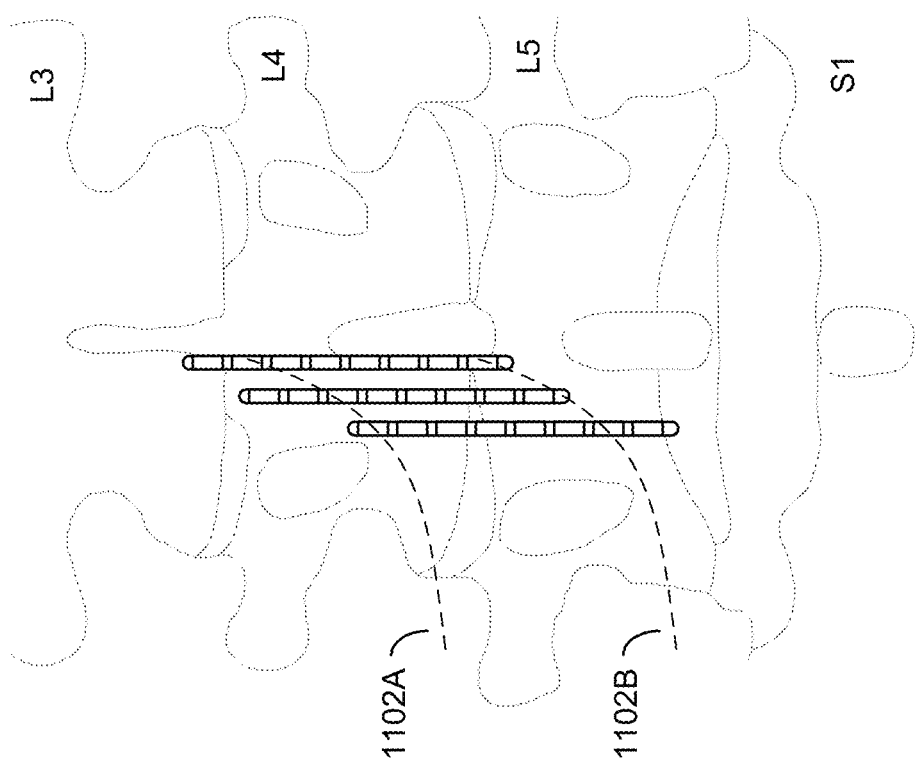
Figure 14:
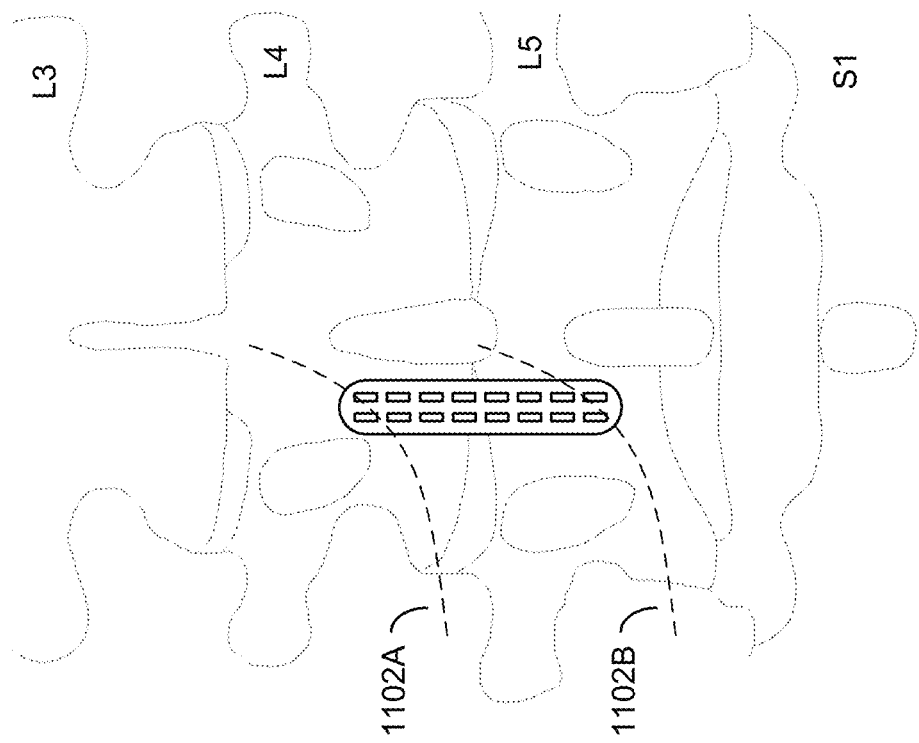
FIGS. 13 and 14 show lateral placements of a four-column paddle lead and a two-column paddle lead, respectively, in the spinal canal in accordance with an aspect of the disclosure.
Figure 13:
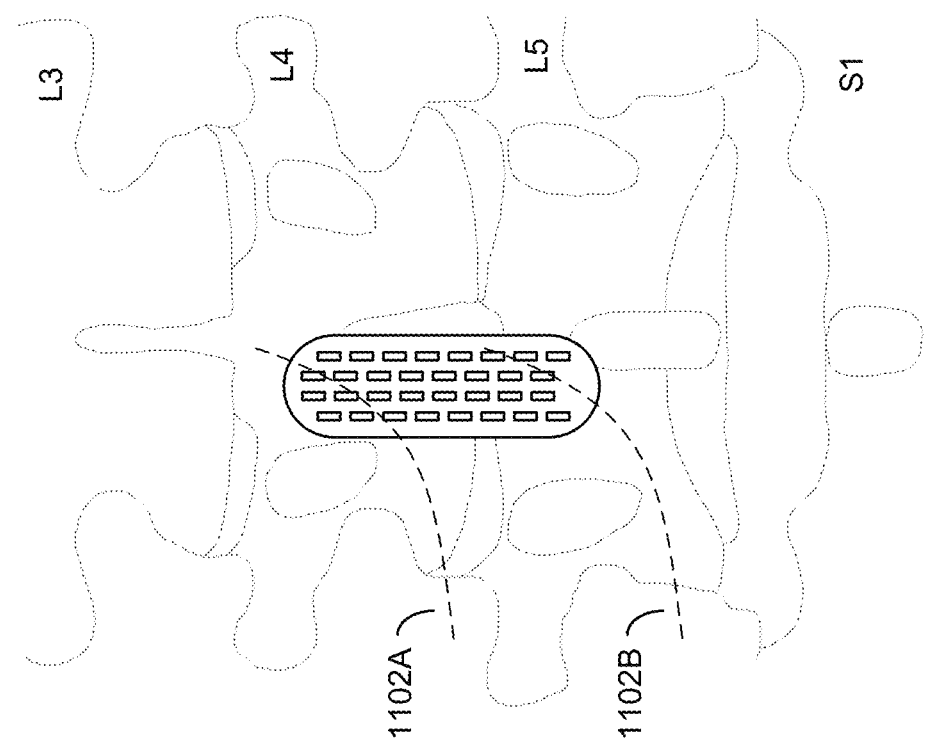
Figure 15:
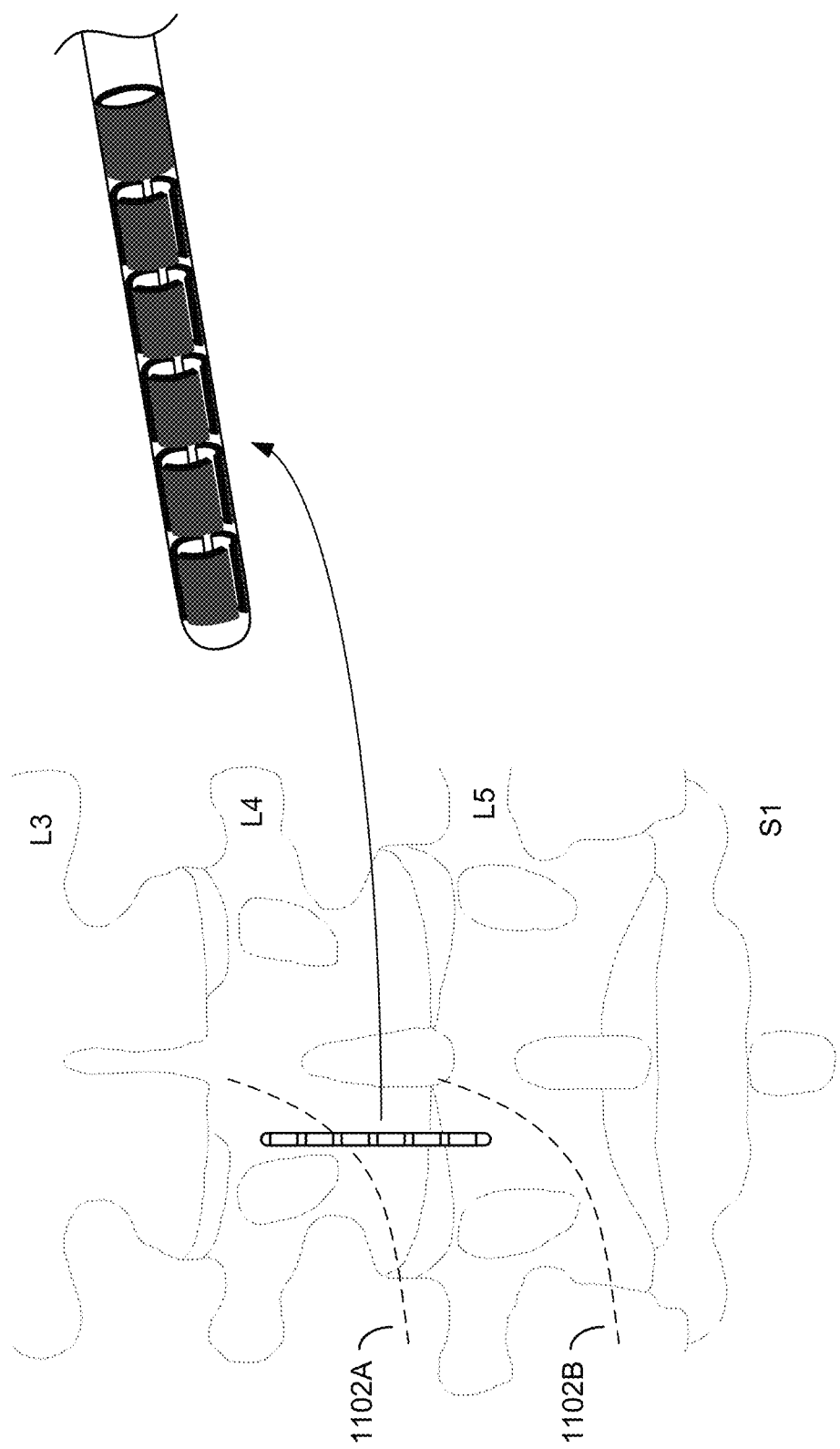
FIG. 15 shows a lateral placement of a single percutaneous lead with segmented electrodes in the spinal canal in accordance with an aspect of the disclosure.

Traditionally, SCS therapy has sought to stimulate dorsal column 1003 fibers while avoiding stimulation of dorsal root 1012 fibers, because stimulation of the dorsal root 1012 fibers at common vertebral electrode implant sites (e.g., T7-T9) is associated with uncomfortable side effects. However, SCS therapies that target different neural fibers, and specifically therapies that target dorsal root 1012 fibers at different vertebral implant locations, are being evaluated. FIGS. 11 through 15 show example lead placements for SCS therapies that target dorsal root 1012 fibers. In FIG. 11, three percutaneous leads 18 are positioned toward the left side of the spinal canal, and in FIG. 12 three percutaneous leads 18 are positioned toward the left side of the spinal canal. In FIG. 13, a single four-column paddle lead 60 is positioned toward the left side of the spinal canal, and in FIG. 14, a single two-column paddle lead is positioned toward the left side of the spinal canal. In FIG. 15, a single percutaneous lead 18 is positioned toward the left side of the spinal canal. Note that the percutaneous lead 18 shown in FIG. 15 includes multiple segmented electrodes that enable lateral control of the stimulation location via a single lead. Moreover, because the segmented electrodes are placed in close lateral proximity, they can be used to provide a high degree of lateral stimulation resolution. While the examples show electrode lead placements to the left side of the spinal canal, lead placements to the right side of the spinal canal are also utilized. As can be seen from the figures, different types of leads with different numbers of electrodes and different electrode spacing (including different types than those shown) can be employed to provide dorsal root stimulation. These example lead placements differ from the placement of leads more proximate to the anatomical midline in traditional SCS therapy.

The above-described current mapping algorithm is tailored to traditional SCS therapy that is targeted at dorsal column 1003 fibers: target poles are aligned vertically around a selected center point of stimulation such that the target stimulation field is aligned with the assumed trajectory of the dorsal column 1003 fibers and stimulation intensity is analyzed using a model that is centered on the anatomical midline and estimates the number of dorsal column 1003 neural elements that are activated for a particular stimulation field. But as the example dorsal root trajectories 1102A and 1102B in FIGS. 11 through 15 show, dorsal root 1012 fibers have different trajectories from dorsal column 1003 fibers, and they are not aligned with the anatomical midline. When stimulation is specifically being targeted to dorsal root fibers, it is desirable to know the locations of the dorsal roots such that stimulation can be customized.

Figure 16:
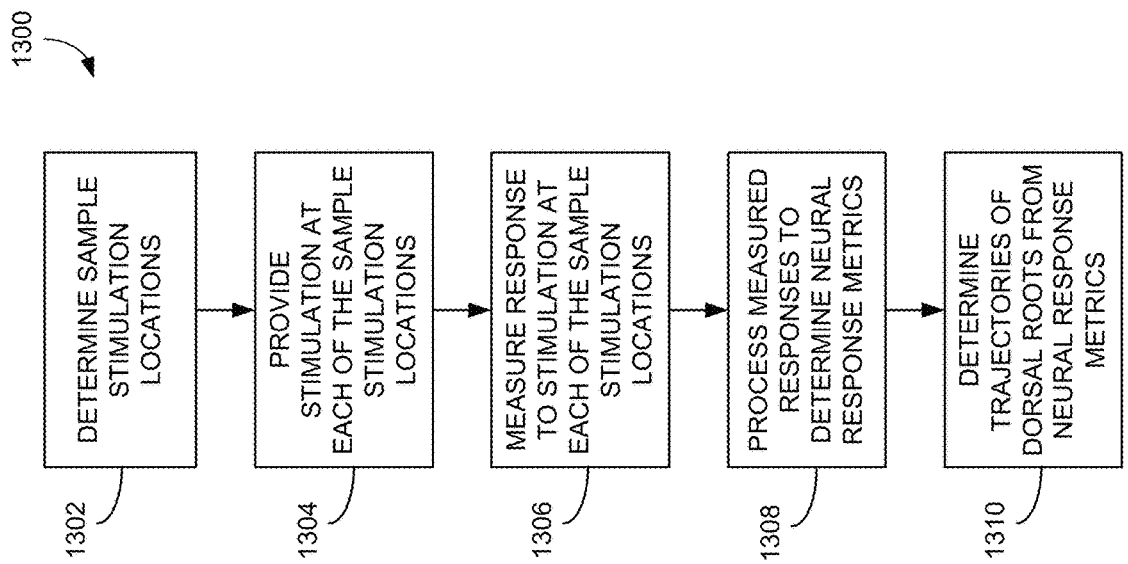
FIG. 16 is a flowchart that shows a neural response process for determining the trajectories of one or more dorsal roots in accordance with an aspect of the disclosure.
Figure 18:
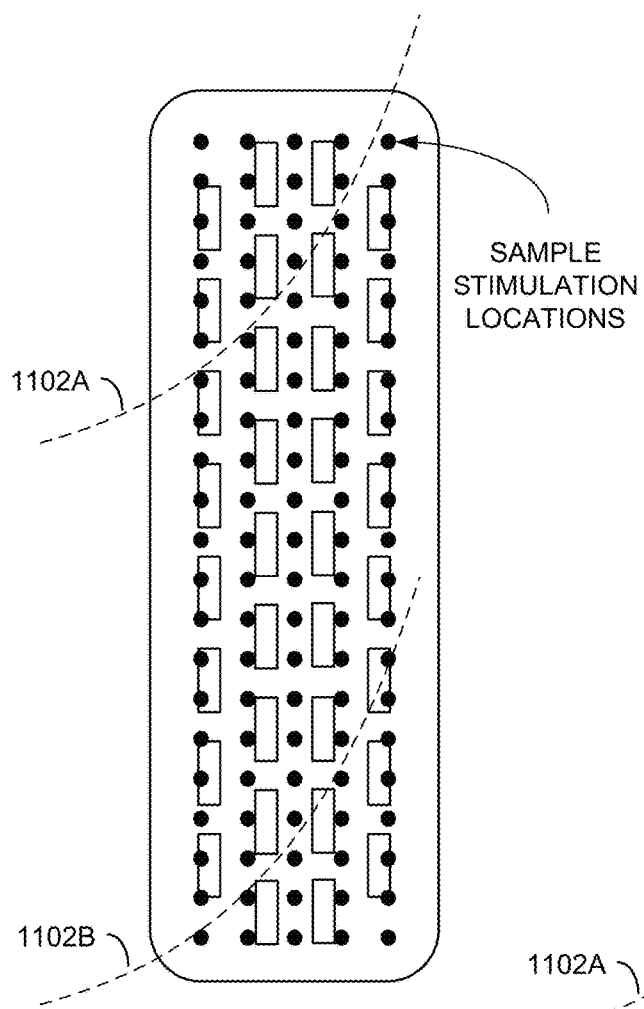
FIG. 18 shows an example of sample stimulation locations that are used in conjunction with the processes shown in FIGS. 16 and 17 in accordance with an aspect of the disclosure.

FIG. 16 is a flowchart that illustrates a neural response process 1300 for determining the trajectories of one or more dorsal roots that are located proximate to implanted electrode leads. The neural response process 1300 measures the patient's neural response to stimulation at a number of sample stimulation locations to estimate the location of dorsal root fibers. The sample stimulation locations are selected as locations that can be reasonably represented by physical electrode allocations (1300). For a single lead configuration (e.g., where a single paddle lead 60 is implanted), the sample stimulation locations may be predetermined as the locations that can be represented via physical electrode allocations using the single lead's electrodes. For multi-lead configurations, the sample stimulation locations may be determined after the leads are implanted and the locations of the electrodes are known (e.g., via placement of the lead representations 406 over the fluoroscopic image 402), because the available sample stimulation locations are dependent upon the location of the electrodes as implanted. The sample stimulation locations may be expressed as a set of coordinates that represent the locations such as in a coordinate system that overlays the fluoroscopic image 402. Each sample stimulation location represents a target stimulation pattern (e.g., a target tripole) and corresponds to a physical electrode allocation (e.g., the physical electrode allocation that is derived from the target stimulation pattern by the current mapping algorithm). The target stimulation patterns for each of the sample stimulation locations are consistent except for the location of the target poles. For example, the target stimulation patterns may each be a target tripole with two equal target anodes that vertically flank a target cathode at a specified focus. In such an embodiment, each sample stimulation location may represent the center point of stimulation of its target stimulation pattern, which is at the target cathode. It will be understood that the stimulation pattern for the sample stimulation locations is a matter of preference and can be configured in any number of manners. FIG. 18 shows an example of a two-dimensional array of sample stimulation locations.

Figure 20:
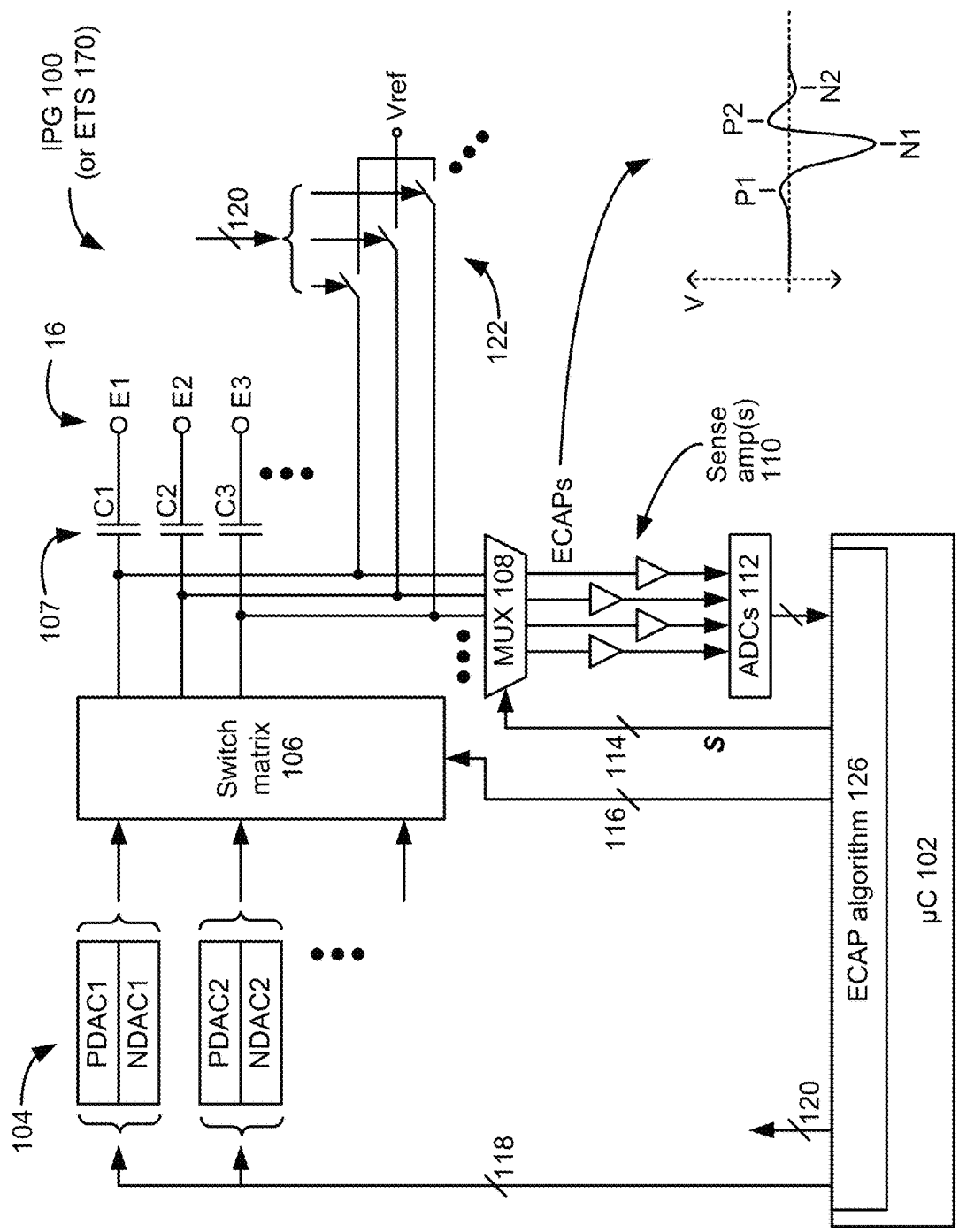
FIG. 20 shows an improved IPG (or ETS) that includes control circuitry programmed with an ECAP algorithm, and further including sensing circuitry for sensing electrical signals at the implanted electrodes in accordance with an example of the disclosure.

Stimulation is then provided at each of the sample stimulation locations (1304), and the patient's neural response to stimulation at each sample stimulation location is measured (1306). When stimulation is delivered, an electric field is generated in the patient's tissue. The generated electric field will cause some of the neural fibers to be recruited and fire, particularly neural fibers proximate to one or more cathodic electrodes. The firing neural fibers create a cumulative response called an Evoked Compound Action Potential, or ECAP, which is shown in FIG. 20 along with circuitry for an improved IPG 100 that includes capability to sense ECAPs. Although described in the context of an IPG 100, it should be realized that stimulation could also be provided and the patient's response measured by an improved external stimulator, such as an External Trial Stimulator 170 that generally mimics the operation of an IPG as explained earlier.

The IPG 100 (or ETS 170) includes control circuitry 102 into which an ECAP algorithm 126 can be programmed. Control circuitry 102 may comprise a microcontroller such as Part Number MSP430, manufactured by Texas Instruments, for example. Other types of control circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs), as described in U.S. Patent Application Publication 2012/0095529 and U.S. Pat. Nos. 9,061,140 and 8,768,453, which are incorporated herein by reference.

In the IPG 100 (or ETS 170) a bus 118 provides digital control signals to one or more Digital-to-Analog converters (DACs) 104, which are used to produce currents or voltages of prescribed amplitudes (A) in accordance with stimulation parameters associated with each of the sample stimulation locations. As shown, the DACs include both PDACs which source current to one or more selected anode electrodes, and NDACs which sink current from one or more selected cathode electrodes. In this example, a switch matrix 106 under control of bus 116 is used to route the output of one or more PDACs and one or more NDACs to any of the electrodes, which effectively selects the anode and cathode electrodes. Buses 118 and 116 thus generally set the stimulation program the IPG 100 is running. The current paths to the electrodes 16 include DC-blocking capacitors 107, which provide additional safety by preventing the inadvertent supply of DC current to an electrode and to a patient's tissue. The illustrated circuitry for producing stimulation pulses and delivering them to the electrodes is merely one example. Other approaches may be found for example in U.S. Pat. Nos. 8,606,362 and 8,620,436, and U.S. Provisional Patent Application Ser. No. 62/393,003, filed Sep. 10, 2016. Note that a switch matrix 106 isn't required, and instead a PDAC and NDAC can be dedicated to (e.g., wired to) each electrode.

Because the neural response estimation process 1300 relies upon a measured neural response to stimulation, each electrode 16 is further coupleable to at least one sense amp 110. In the example shown, there are four sense amps 110 but more or fewer could be employed in alternate configurations. Under control by bus 114, a multiplexer 108 can couple any of the electrodes to any of the sense amps 110 at a given time. This is however not strictly necessary, and instead each electrode can be coupleable to its own dedicated sense amp 110, or all electrodes can be selected for sensing at different times and presented by MUX 108 to a single sense amp 110. The analog waveform comprising the ECAP is preferably converted to digital signals by one or more Analog-to-Digital converters (ADC(s)) 112, which may sample the waveform at 50 kHz for example. The ADC(s) may also reside within the control circuitry 102, particularly if the control circuitry 102 has A/D inputs. The connection of the electrodes 16 to the sense amp(s) 110 preferably occurs through the DC-blocking capacitors 107, such that capacitors are between the electrodes and the sense amp(s) 110. This is preferred so as to not undermine the safety provided by the DC-blocking capacitors 107.

Figure 19:
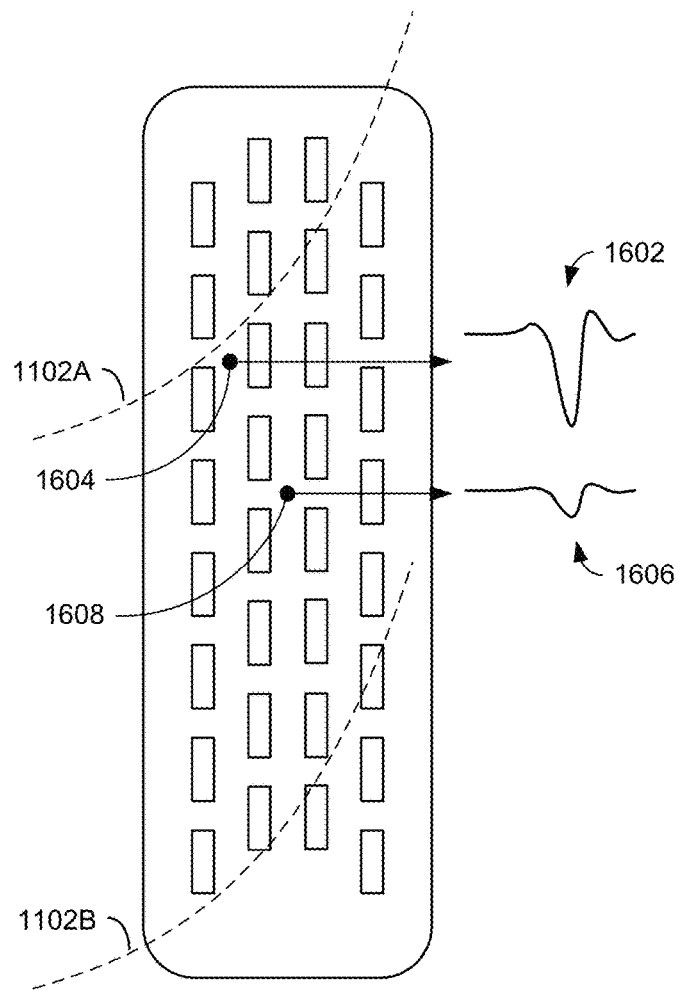
FIG. 19 shows the difference between example ECAP responses that are measured for stimulation that is nearer and further from a dorsal root in accordance with an example of the disclosure.

Once the digitized ECAP is received at the control circuitry 102, it is processed by the ECAP algorithm 126 to determine the magnitude of the neural response induced by stimulation. The magnitude of the ECAP can be specified in different ways such as the magnitude of its peak N1, its integral over time, etc., as long as magnitude is determined consistently across all of the sample stimulation locations. When stimulation is provided nearer to dorsal root fibers where neural fiber density is higher, the magnitude of an ECAP that is observed at other electrodes will be greater because the ECAP's magnitude is proportional to the number of neural fibers that are firing. For example, as shown in FIG. 19, the ECAP 1602 generated as a result of stimulation having a first stimulation location 1604 has a greater magnitude than the ECAP 1606 generated as a result of stimulation having a second stimulation location 1608 due to the first location 1604's proximity to the dorsal root fibers shown by trajectory 1102A.

Generally speaking, a primary ECAP response, e.g., the height of peak N1, can vary, usually between microVolts to tens of milliVolts. Note that the DC blocking capacitor 107 through which the ECAPs pass will remove any DC components in the signal, which is thus referenced to 0 Volts. If necessary, the sensed ECAP signal can be amplified and level-shifted by the sense amp(s) 110 so that its voltage is brought within a range that the control circuitry 102 and/or ADCs 112 can handle, such as between 3 volts and ground.

Because ECAPs travel up and down the spinal cord, they can be observed at essentially any electrode for a given sample stimulation location. In one embodiment, the ECAP is measured at multiple different electrodes 16 for each of the sample stimulation locations. The measured one or more ECAPs that are associated with a sample stimulation location are evaluated and their properties (e.g., magnitude, shape, etc.) may be stored in a memory in the neurostimulator or communicated to the CP computer 202. The process of providing stimulation at each of the sample stimulation locations and measuring the response continues until stimulation has been provided and ECAP responses measured for all of the sample stimulation locations. In one embodiment, the stimulation and measurement parameters other than the stimulation location (i.e., other than electrode allocation) are held constant for each of the sample stimulation locations. For example, the stimulation amplitude, frequency, pulse width, duration, etc. and the one or more electrodes at which the response is measured are held consistent across the full set of sample stimulation locations.

When the patient's neural response to stimulation at each of the sample stimulation locations has been determined (e.g., measured by the neurostimulator and communicated to an external device such as CP computer 202), the measurements may be processed to determine a neural response metric that is comparable across different spatial locations (1308). For example, the one or more ECAP magnitude values that are recorded for a particular sample stimulation location may be adjusted to compensate for the distance between the stimulation location and the sense electrode as ECAP signals attenuate with distance from the stimulation location. Similarly, where ECAPs are measured at multiple electrodes for a single stimulation location, the measured responses may be averaged or otherwise processed to compute a single neural response metric for the sample stimulation location. In one embodiment, additional properties of the measured ECAPs may be evaluated to determine a neural response metric for a sample stimulation location. For example, because the shape of an ECAP signal is influenced by the population of neurons that are recruited, the shape of measured ECAP signals and their associated delays may be evaluated. By way of example, two different stimulation locations may both elicit ECAP signals having the same magnitude but one ECAP signal may have a shape that is indicative of undesirable stimulation (e.g., motor neuron stimulation) while the other ECAP signal may have a shape that is indicative of desirable stimulation. These shapes may therefore be evaluated to determine a neural response metric that is indicative of a degree of desirable stimulation for each of the sample stimulation locations.

The determined neural response metrics form a neural response map in which each sample stimulation location has an associated neural response metric. The neural response map represents the magnitude of the patient's neural response to stimulation (or the magnitude of the desirability of the response) across a two-dimensional space. From the neural response map, the dorsal root trajectories such as trajectories 1102 can be identified as the local maxima in the two-dimensional space (1310). In one embodiment, the dorsal root trajectories may be determined automatically from the neural response metrics (e.g., by taking the derivative of the neural response metrics in each of the two spatial dimensions). In such an embodiment, the determined dorsal root trajectories can be verified against the fluoroscopic image 402 (e.g., either manually or through image recognition) to verify that the determined dorsal root trajectories are anatomically sensible. In another embodiment, the neural response map may be presented to a clinician (e.g., through the interface 94), and the clinician may specify (e.g., trace) the dorsal root trajectories based on the neural response map and the fluoroscopic image 402. In such an embodiment, the neural response map may be presented as a contour map (e.g., with values depicted by color) that is overlaid on the fluoroscopic image 402. The trajectories of the one or more dorsal roots may be expressed as equations in the two-dimensional space, which equations can be determined via curve fitting techniques. In one embodiment, the trajectories of the one or more dorsal roots are shown on a user interface such as the interface 94 (or 94' described below).

The measured ECAP signal can also be used to identify the location of other anatomical features. For example, ECAP magnitude (e.g., N1 to P2 amplitude) is sensitive to the location of intervertebral disks. Thus, regardless of the stimulation location, ECAP signals that are measured at locations near intervertebral disks have a lower magnitude. By evaluating the measured ECAP responses (perhaps in conjunction with the fluoroscopic image 402), the location of intervertebral disks can be determined. From the locations of the intervertebral disks and the dorsal root trajectories, the locations of the dorsal root ganglia, which reside in the neural foramen, can be estimated. As will be described below, the soma that form the dorsal root ganglia can be modeled differently from other neural fibers.

Figure 17:
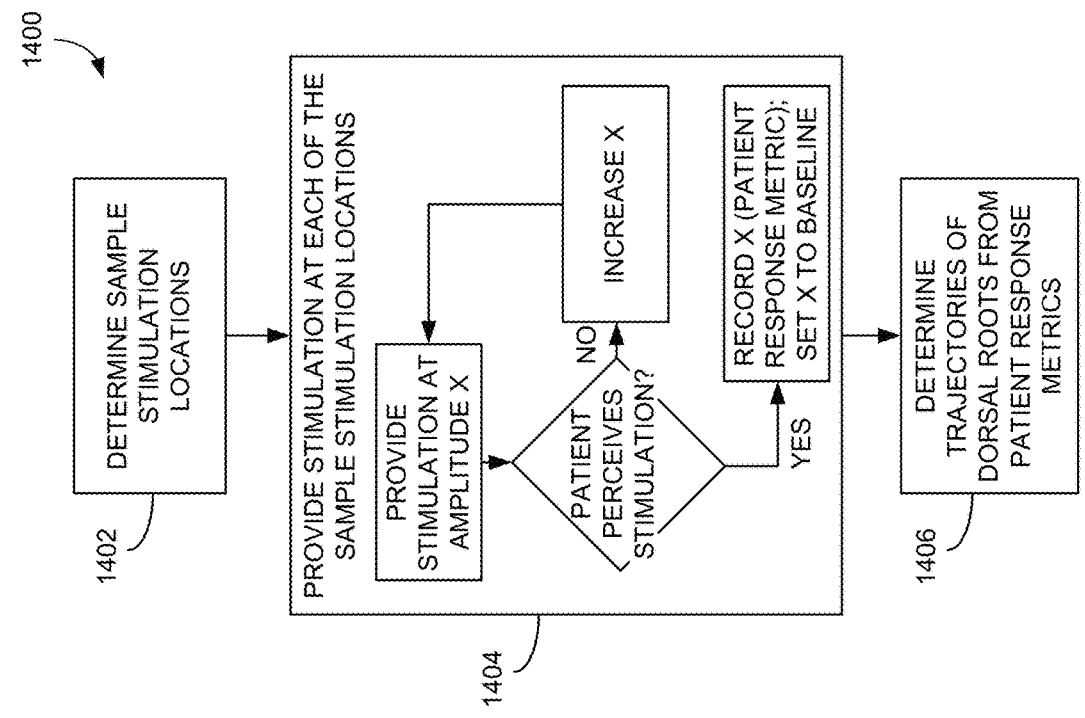
FIG. 17 is a flowchart that shows a patient response process for determining the trajectories of one or more dorsal roots in accordance with an aspect of the disclosure.

FIG. 17 is a flowchart that illustrates a patient response process 1400 for determining the trajectories of one or more dorsal roots that are located proximate to implanted electrode leads. The patient response process 1400 utilizes a stimulation threshold response provided by the patient to stimulation at a number of sample stimulation locations to estimate the dorsal root trajectories. The sample stimulation locations are determined in the same manner as described above with respect to the neural response process 1300 (1402). As with the neural response process 1300, stimulation is provided at each of the sample stimulation locations (1404). In the patient response process 1400, though, at each of the sample stimulation locations, stimulation is initially provided at a low amplitude (e.g., 0.5 mA) and the stimulation amplitude is increased until the patient indicates that he or she perceives the stimulation. When the stimulation location is nearer to a dorsal root, more neural fibers fire at a given stimulation amplitude and thus the stimulation perception threshold is lower (i.e., the patient perceives stimulation at a lower stimulation amplitude) than at stimulation locations further removed from a dorsal root. The determined stimulation perception threshold measurements (which can be recorded for example as the stimulation amplitude at which stimulation is perceived) can then be processed to form a patient response map that represents the patient's stimulation perception threshold across a two-dimensional space. In one embodiment, a level of undesirable side effects of stimulation may also be recorded by the patient. In such an embodiment, the measure of undesirable side effects may be utilized to adjust the stimulation perception threshold measurements such that the stimulation perception threshold measurements represent the level of desirable stimulation. In addition to stimulation perception thresholds, the patient response map may include textual notes provided by a clinician and associated with a particular stimulation location. For example, a clinician may note the anatomical location of stimulation perception (e.g., foot, knee, hip, etc.) for different stimulation locations across the two-dimensional map.

From the patient response map, the dorsal root trajectories such as trajectories 1102 can be identified as the local minima in the two-dimensional space (1406). In one embodiment, the dorsal root trajectories may be determined automatically based on the patient response map (e.g., by taking the derivative of the patient response metrics in each of the two spatial dimensions). In such an embodiment, the determined dorsal root trajectories can be verified against the fluoroscopic image 402 (e.g., either manually or through image recognition) to verify that the determined dorsal root trajectories are anatomically sensible. In another embodiment, the patient response map may be presented to a clinician, and the clinician may specify (e.g., trace) the dorsal root trajectories based on the patient response map and the fluoroscopic image 402. In such an embodiment, the patient response map may be presented as a contour map (e.g., with values depicted by color) that is overlaid on the fluoroscopic image 402. The trajectories of the one or more dorsal roots may be expressed as equations in the two-dimensional space, which equations can be determined via curve fitting techniques. In one embodiment, the trajectories of the one or more dorsal roots are shown on a user interface such as the interface 94 (or 94' described below). As with the neural response process 1300, the patient response map can also be utilized to estimate the location of anatomical features such as the pedicles and, ultimately, the dorsal root ganglia. It should be noted that the patient response process 1400 does not require sensing capability in the IPG and can therefore be utilized with existing IPGs that do not include sensing capability.

While the neural response process 1300 and the patient response process 1400 have been described in terms of the provision of stimulation at each of the sample stimulation locations, in other embodiments of these processes, stimulation may be provided at only a subset of the sample stimulation locations. For example, stimulation may be provided at each of the sample stimulation locations in a single column and the location of one or more dorsal roots' intersection with that column of sample stimulation points can be determined (in the same manner as described above for the different processes 1300 and 1400). Stimulation may then be provided at stimulation points in neighboring columns near the determined locations of the one or more dorsal roots according to the assumed slope of the one or more dorsal roots. For example, it may not be necessary to provide stimulation at a sample stimulation location that is inferior and medial to a determined dorsal root location. In addition, stimulation may be provided at a higher spatial resolution near the determined dorsal root locations. In this way, stimulation may be provided at only a subset of the sample stimulation points.

The neural and patient response dorsal root trajectories processes 1300 and 1400 are primarily executed on the CP computer 202 such as through the execution of CP software 96. However, as will be understood, the CP computer 202 that is performing the root trajectory process 1300 or 1400 must interact with the neurostimulator device (e.g., the IPG or ETS). For example, CP software 96 may include instructions to determine the sample stimulation locations, determine the electrode configurations that correspond to the desired stimulation locations (e.g., via current mapping algorithm), process the neural or patient responses to determine the trajectories of the dorsal roots, etc. However, the CP computer 202 must also provide instructions to the neurostimulator such that stimulation can be provided according to the desired parameters to evaluate the patient's response. For example, the CP computer 202 may send instructions (e.g., electrode configuration, stimulation frequency, etc.) via communication link 92 to cause the neurostimulator to provide stimulation. The CP computer 202 may also send instructions to cause the neurostimulator to record one or more ECAP signals. In one embodiment, the instructions are provided to the neurostimulator in bulk. For example, for the neural response process 1300, the CP computer 202 may send a set of instructions to cause the neurostimulator to provide stimulation according to a number of different sets of parameters (e.g., sample stimulation locations), to record the ECAP signals induced by stimulation using each of the different sets of parameters at one or more electrodes, and to report the measured ECAP amplitudes back to the external device. In such an embodiment, the neurostimulator may be pre-programmed with a dorsal root estimation routine (e.g., as part of ECAP algorithm 126) and the instructions from the CP computer 202 may simply invoke execution of that routine using a supplied set of parameters. Alternatively, the CP computer 202 may provide more discrete instructions. For example, rather than providing a bulk set of instructions and then waiting for the neurostimulator to execute the instructions and provide a response, the CP computer 202 may provide a single set of stimulation parameters (corresponding to stimulation at a single sample stimulation location) and instructions to measure the resulting ECAP at one or more electrodes and to report the measured ECAP magnitude. In such an embodiment, upon receipt of the ECAP magnitude, the CP computer 202 may transmit a subsequent single set of stimulation parameters (corresponding to stimulation at a different sample stimulation location) and instructions to measure the resulting ECAP at one or more electrodes and to report the measured ECAP magnitude.

Figure 21:
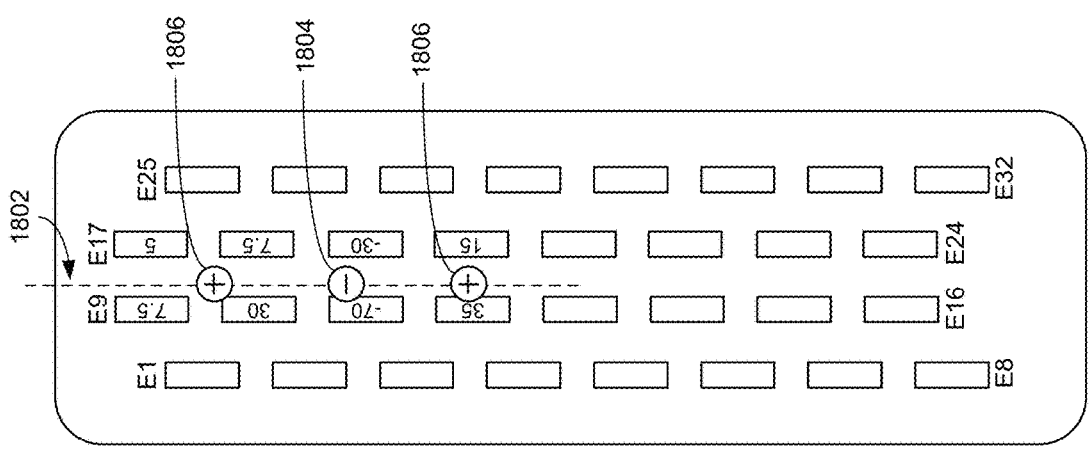

The current mapping algorithm described above can be improved in two significant ways based on the determined trajectory of one or more dorsal roots: the target stimulation field can be constructed to lie along a path that is substantially parallel with the nearest dorsal root (i.e., the fibers that are intended to be stimulated) and neural element evaluation positions can be located along one or more paths that are substantially parallel with the dorsal roots. FIG. 21 shows the construction of a target stimulation field along a line 1802 that is parallel with the anatomical midline in accordance with traditional SCS therapy. As described above, the user specifies a center point of stimulation and a focus. As FIG. 21 shows, based on these inputs, the current mapping algorithm models the electric potentials that would be generated as a result of stimulation at a 100% cathode 1804 located at the specified center point and two equal (50%) anodes 1806 that are located at the specified focus distance directly above and below (i.e., parallel with the anatomical midline) the cathode 1804. Given the locations of the physical electrodes, the current mapping algorithm determines that the target stimulation field formed by these target poles is best represented when the anodic current is allocated to electrodes E9 (7.5%), E10 (30%), E12 (35%), E17 (5%), E18 (7.5%), and E20 (15%) and the cathodic current is allocated to electrodes E11 (70%) and E19 (30%).

However, as described above, in newer SCS therapies when the leads are implanted more laterally, stimulation is directed at the dorsal root fibers. Thus, when the user specifies a center point of stimulation and focus, the user is indicating a desired location and breadth of stimulation along or substantially parallel with the dorsal root. That is, the center point of stimulation is intended to specify an offset from the dorsal root and the focus is intended to specify the breadth of the stimulation field along a path that is substantially parallel with the dorsal root. Based on the determined trajectories of the one or more dorsal roots, the specified center point of stimulation and focus can be utilized to determine an electrode configuration that causes the stimulation field to be substantially parallel with the dorsal root that is closest to the specified center point of stimulation, which more closely matches the user's intent.

Figure 22:
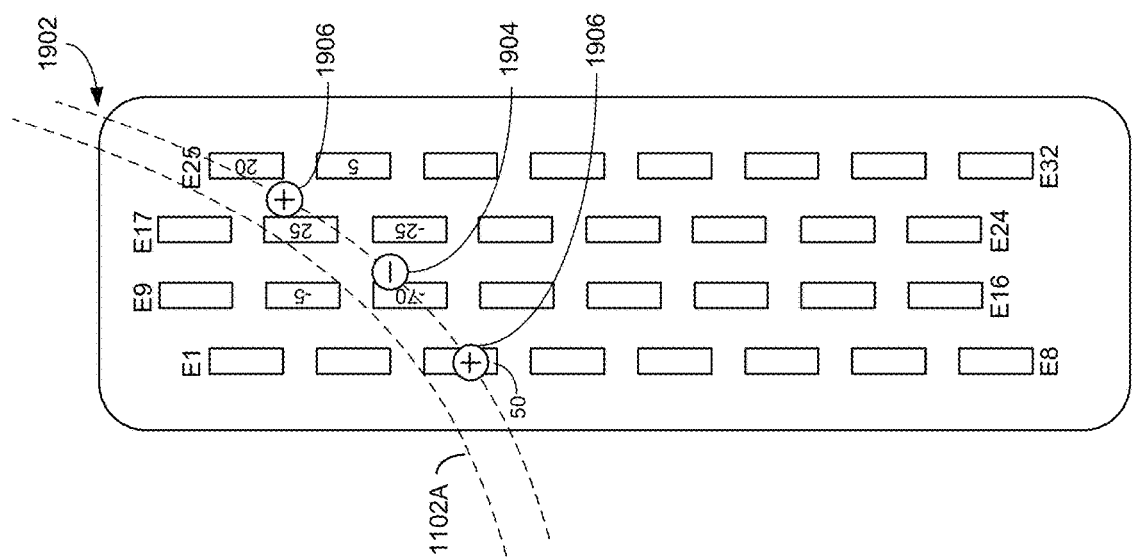
FIGS. 21 and 22 show the generation of a target stimulation field that is parallel with the anatomical midline and a dorsal root trajectory, respectively, in accordance with an example of the disclosure.

FIG. 22 shows the construction of a target stimulation field along a path 1902 that is parallel with the trajectory 1102A of the dorsal root that is nearest to the specified center point of stimulation in accordance with an improved current mapping algorithm. The specified center point of stimulation and focus are the same in FIG. 22 as in FIG. 21. However, based on the determined trajectories of the one or more dorsal roots, the improved current mapping algorithm models the electric potentials that would be generated as a result of stimulation at a 100% cathode 1904 located at the specified center point and two equal (50%) anodes 1906 that are located at the specified focus distance away from the cathode along the path 1902. The trajectories of the one or more dorsal roots can be represented by equations in a two-dimensional coordinate system as described above, so the parameters (e.g., the equation specifying the determined trajectory) of the trajectory of the dorsal root nearest to the selected center point of stimulation are known. Due to the curve of the determined dorsal root trajectory 1102A, the target poles 1904 and 1906 are not collinear. In one embodiment, determining the location of the target anodes involves translating the determined trajectory of the dorsal root nearest to the selected center point of stimulation along the shortest path between the trajectory and the center point of stimulation such that the translated trajectory intersects the selected center point and calculating the locations of the target anodes as the points that are the specified focus distance away from the center point in each direction along the translated trajectory based on the equation of the translated trajectory.

As illustrated in FIG. 22, the changes to the target stimulation field result in a different allocation of current among the electrodes than that in FIG. 21. Specifically, the target stimulation field that is modeled by the improved current mapping algorithm is best represented when the anodic current is allocated to electrodes E3 (50%), E18 (25%), E25 (20%), and E26 (5%) and the cathodic current is allocated to electrodes E10 (5%), E11 (70%), and E19 (25%). Therefore, the improved current mapping algorithm provides a different allocation of current among electrodes that more closely represents the intended stimulation field. The determined electrode configuration, which can specify a polarity and amplitude of stimulation for the electrodes (e.g., a stimulation magnitude for the utilized electrodes or a total stimulation amplitude and an allocation fraction for the utilized electrodes) can be communicated to the neurostimulator (e.g., to the IPG or ETS via communication link 92) to enable the neurostimulator to generate the stimulation field.

Figure 23:
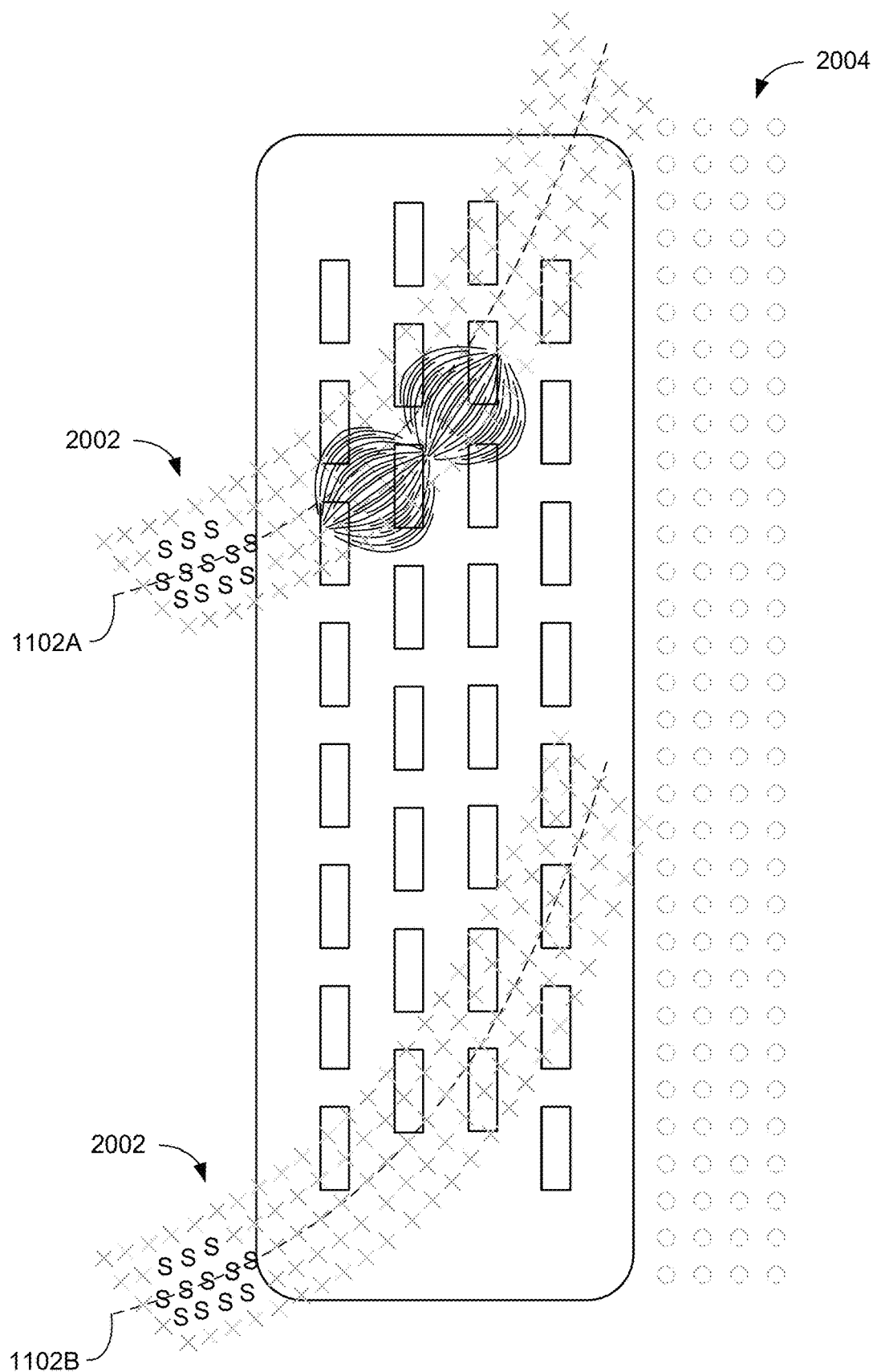
FIG. 23 shows a neural model that includes neural response evaluation positions that are parallel with one or more dorsal roots in accordance with an example of the disclosure.

In addition to constructing the target field along a path that is substantially parallel with the trajectory of the dorsal root that is nearest to the selected center point of stimulation, dorsal root neural element evaluation positions 2002 that are substantially parallel with the determined trajectories 1102 of the one or more dorsal roots are included in the neural element model as illustrated in FIG. 23. In FIG. 23, dorsal root neural element evaluation positions 2002 are marked with 'X' and dorsal column neural element evaluation positions 2004, which are still included in the illustrated embodiment of the neural element model, are marked with 'O'. In addition, soma neural element evaluation positions of the dorsal root ganglia, the location of which can be estimated as described above, are marked with 'S'. The various neural elements may be modeled differently according to their unique properties. The locations of the dorsal root evaluation positions 2002 may be determined in a similar manner to the determination of the location of target poles as described above. For example, the locations of dorsal root evaluation positions 2002 may be calculated for a desired inter-position spacing based on the equations that represent the determined trajectories 1102 of the one or more dorsal roots. In the illustrated embodiment, the dorsal root neural element evaluation positions 2002 are arranged in grids that are aligned with the determined dorsal root trajectories 1102. The dorsal root grids span the assumed breadth of the dorsal root fibers, which breadth may be assumed constant for all patients or estimated based on the fluoroscopic image 402. In the illustrated embodiment, the dorsal column neural element evaluation positions 2004 are arranged in a grid that is aligned with the anatomical midline. The dorsal column grid spans the assumed breadth of the dorsal column fibers, which breadth may be assumed constant for all patients or estimated based on the fluoroscopic image 402. Inclusion of the dorsal root neural element evaluation positions 2002 in the neural element model increases the model's accuracy as it accounts for the activation of dorsal root fibers that were not previously considered in the neural element model. As a result, the volume of activation can be more accurately determined.

Figure 24:
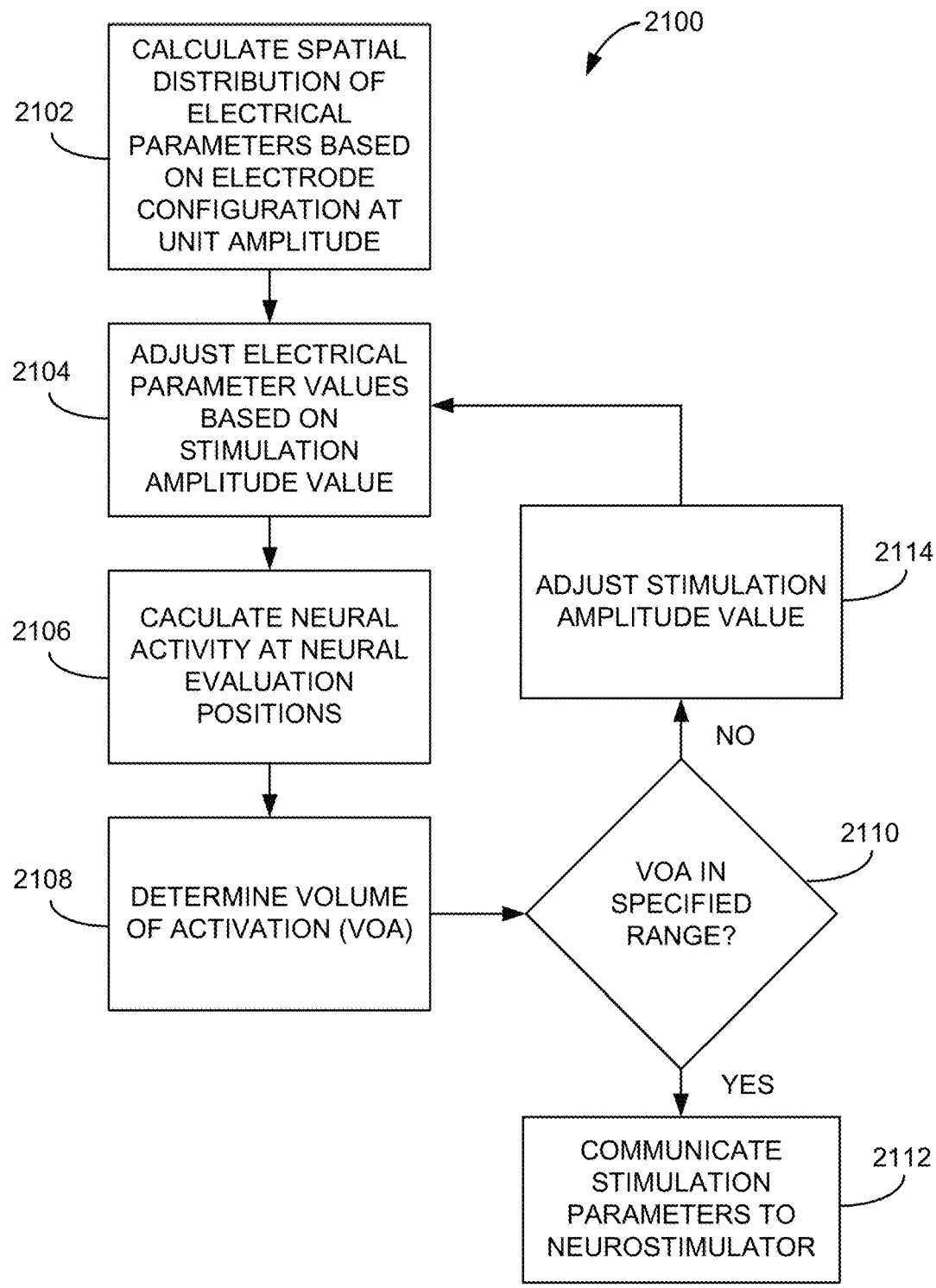
FIG. 24 is a flowchart that shows a process for maintaining a stimulation intensity that utilizes neural element modeling at evaluation positions that are parallel with one or more dorsal roots in accordance with an example of the disclosure.

FIG. 24 is a flowchart that illustrates an improved stimulation amplitude adjustment process. The stimulation amplitude adjustment process 2100 is performed after the determination of the electrode allocation for a target stimulation field (e.g., a target stimulation field that is parallel with the trajectory of a dorsal root), and the electric field model that was described above is used to determine the spatial distribution of electrical parameters (e.g., electric potentials, electric field strength, current density, etc.) based on stimulation using the determined electrode allocation at unit amplitude (e.g., 1 mA) (2102). The modeled electrical parameters are then adjusted from the unit amplitude base values according to the stimulation amplitude value (2104). Initially, the stimulation amplitude value may be the present stimulation amplitude setting that is being used (e.g., 5.0 mA). FIG. 23 illustrates an example of an electric field 2006 that is generated using the electrode allocation described with respect to FIG. 22 at an example stimulation amplitude. The electrical parameter values may be assumed to scale linearly with increasing amplitude and thus the values determined for unit current may be multiplied by a scaling factor as opposed to repeating the electric field modeling for the new stimulation amplitude.

The response to stimulation is then determined at the neural element evaluation positions (2106). As described above, the neural element evaluation positions include dorsal root evaluation positions 2002 that are aligned with the determined trajectories of one or more dorsal roots and dorsal column evaluation positions 2006 that are aligned with the patient's anatomical midline.

The electrical parameters at each of the neural element evaluation positions are input to a neural element model that determines the response to the stimulation of neural elements positioned at the evaluation position. In one embodiment, the neural element model takes into account the morphological and electrical properties of various neural elements to estimate the response of the neural elements to electrical stimulation. The neural element model may estimate the transmembrane potentials (and/or other related parameters) that would be induced in the neural elements as a result of the modeled electric potential field. Neural activation may be determined based on an activating function (i.e., the $2^{nd}$ spatial derivative of the electrical potentials along an axis of the neural elements (which axis is parallel with the dorsal root trajectory 2002 for dorsal root evaluation positions 2002 and parallel with the anatomical midline for dorsal column evaluation positions 2004), a driving function (i.e., a weighted average of the activating function at a node of Ranvier and those at adjacent nodes along the neural elements), or a $1^{st}$ spatial derivative of the electrical potentials along an axis of the neural elements. Neural activation may also be evaluated using a priori machine learning techniques. In one embodiment, the neural element model accounts for differences in dorsal root fibers and dorsal column fibers and thus differently determines whether activation occurs at a dorsal root evaluation position 2002 and a dorsal column evaluation position 2004. Based on the results of the neural model as applied at each of the neural element evaluation positions, the quantity of neural elements that would be activated (or the volume of activation) can be determined (2108).

It is then determined whether the volume of activation is within a specified range (2110). The specified range may be a range that encompasses a volume of activation that was determined to be acceptable for the patient (e.g., the volume of activation that is associated with an initial acceptable set of stimulation parameters). If the volume of activation is within the specified range, the electrode configuration and any additional stimulation parameters are communicated from the CP computer 202 to the neurostimulator (e.g., the IPG or ETS via communication link 92) such that stimulation in accordance with the specified parameters may be delivered to the patient (2112). If, however, the modeled response of neural elements deviates from a desired response (i.e., the volume of activation is not within the specified range), the stimulation amplitude is either increased or decreased to bring the volume of activation towards the specified range (2114). In one embodiment, the stimulation amplitude value is increased by a fixed percentage of the present value. In another embodiment, the magnitude of the stimulation amplitude value adjustment is determined based on the difference between the determined volume of activation and the specified range. The modeled electrical parameter values are then updated based on the adjusted stimulation amplitude (2104) and the process continues iteratively until the volume of activation is determined to be within the specified range.

Figure 25:
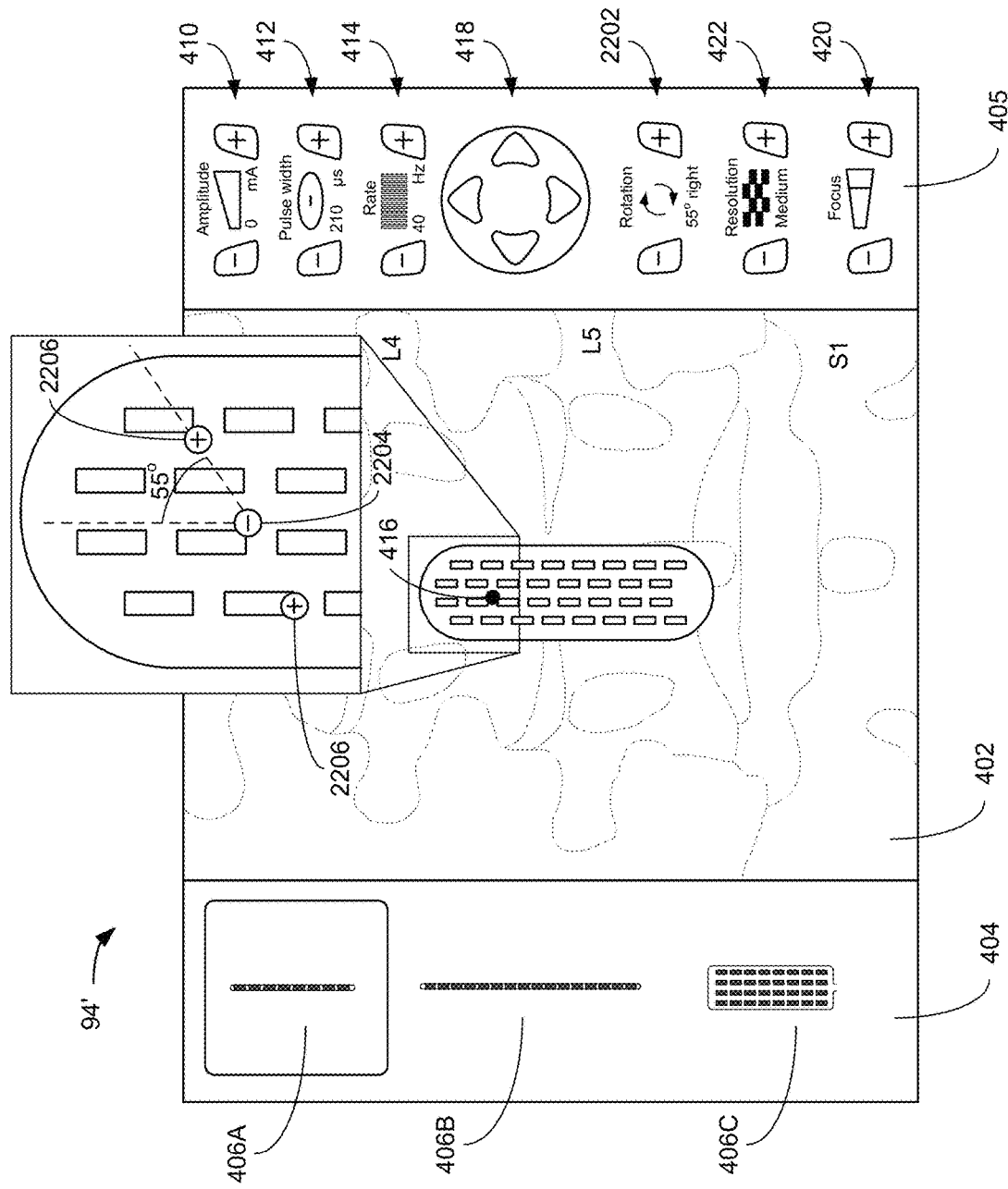
FIG. 25 shows an improved interface that enables rotation of a target stimulation field in accordance with an example of the disclosure.

While the disclosure has to this point described techniques for determining the trajectory of one or more dorsal root fibers and providing stimulation that is aligned with the determined trajectory, target stimulation fields can also be manually adjusted to more precisely target dorsal root fibers. FIG. 25 illustrates an improved interface 94' that includes a rotation adjuster 2202 in the stimulation interface 405. The rotation adjuster 2202 enables the user to rotate the target stimulation field about the selected center point of stimulation 416. When no rotation is selected, the target field is aligned vertically. However, when the user uses the rotation adjuster 2202 to rotate the stimulation field, the target field is rotated about the selected center point 416 by the desired amount. In the embodiment illustrated in FIG. 25, the target stimulation field is represented by a target tripole in which the two equal target anodes 2206 flank a single target cathode 2204. As shown in the enlarged portion of FIG. 25, the target anodes are rotated 55 degrees right of vertical based on the rotation entered via the rotation adjuster 2202. The rotation adjuster 2202 enables stimulation to be targeted to dorsal root fibers even where it is not practical to determine the trajectory of dorsal root fibers. For example, the user can move the center point of stimulation 416 to a desired location (e.g., a location that provides pain relief) using the arrows 418 with no rotation and can then rotate the target stimulation field about the center point of stimulation 416 using the rotation adjuster 2202 to customize the therapy to target dorsal root fibers. The rotation amount can be selected based on the patient's preference (i.e., the rotation that provides the most significant pain relief). The fluoroscopic image 402 is particularly beneficial in this type of manual-adjustment configuration because the center point of stimulation 416 can be positioned laterally between adjacent vertebrae to provide a good initial estimate of the dorsal root location. Although not illustrated, the interface 94' may additionally include a selector to specify whether target fields should be generated for dorsal column stimulation (e.g., vertical orientation) or dorsal root stimulation (e.g., orientation parallel to determined trajectories of one or more dorsal roots). As will be understood, selection of dorsal root stimulation may present a further interface that enables the user to initiate the process of determining the trajectories of one or more dorsal roots such as via the process 1300 or 1400.

Figure 26:
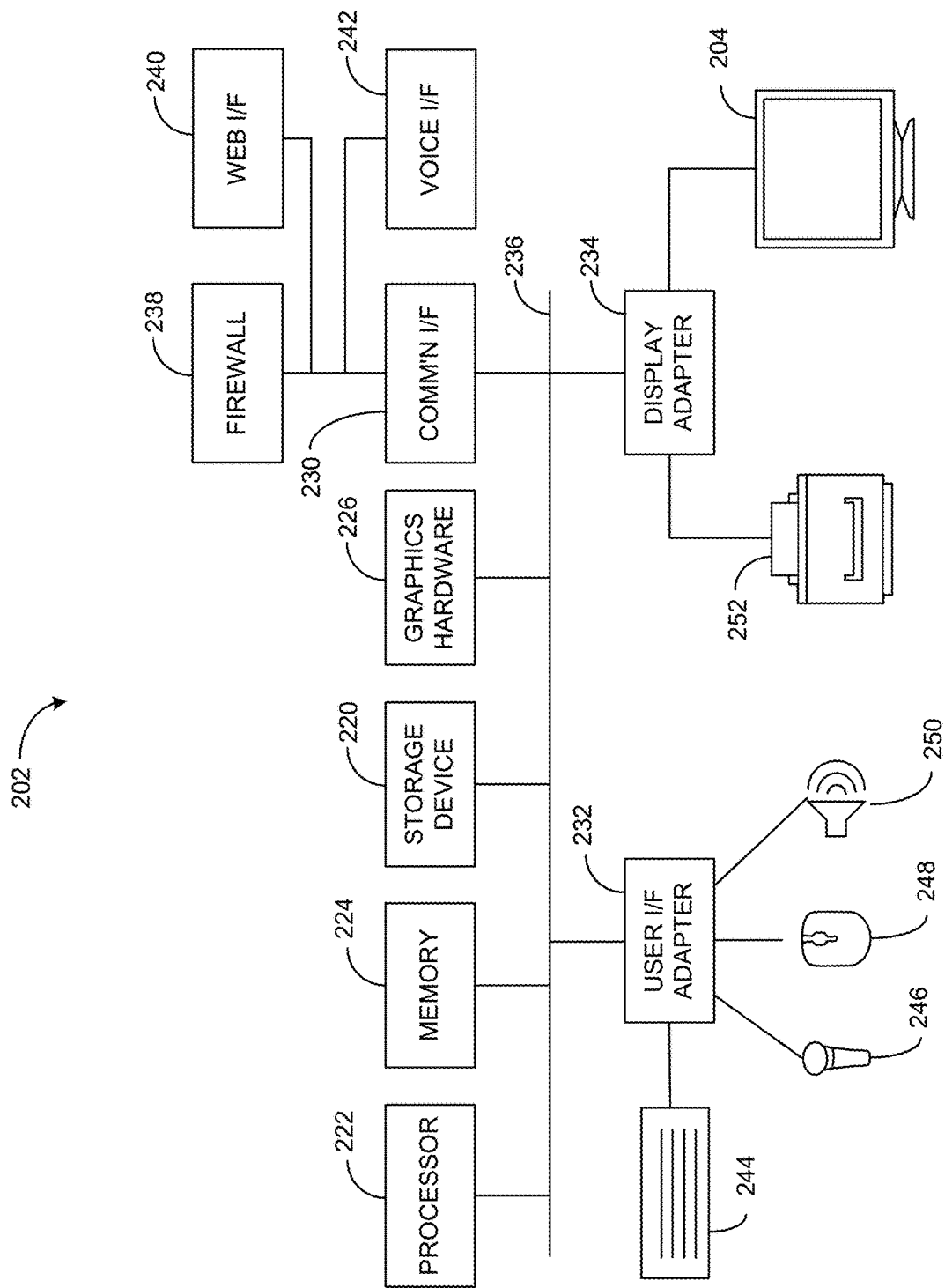
FIG. 26 illustrates a representative computing environment on which software that is associated with one or more aspects of the disclosure may be executed.

FIG. 26 illustrates the various components of an example CP computer 202 that may be configured to execute CP software 96. The CP computer 202 can include the processor 222, memory 224, storage 220, graphics hardware 226, communication interface 230, user interface adapter 232 and display adapter 234—all of which may be coupled via system bus or backplane 236. Memory 224 may include one or more different types of media (typically solid-state) used by the processor 222 and graphics hardware 226. For example, memory 224 may include memory cache, read-only memory (ROM), and/or random access memory (RAM). Storage 220 may store media, computer program instructions or software (e.g., CP software 96), preference information, device profile information, and any other suitable data. Storage 220 may include one or more non-transitory computer-readable storage mediums including, for example, magnetic disks (fixed, floppy, and removable) and tape, optical media such as CD-ROMs and digital video disks (DVDs), and semiconductor memory devices such as Electrically Programmable Read-Only Memory (EPROM), Electrically Erasable Programmable Read-Only Memory (EEPROM), and USB or thumb drive. Memory 224 and storage 220 may be used to tangibly retain computer program instructions or code organized into one or more modules and written in any desired computer programming language. As will be understood, the CP software 96 may be stored on a medium such as a CD or a USB drive, pre-loaded on a computing device such as the CP computer 202, or made available for download from a program repository via a network connection. Communication interface 230 (which may comprise, for example, the ports 206 or 208) may be used to connect the CP computer 202 to a network. Communications directed to the CP computer 202 may be passed through a protective firewall 238. Such communications may be interpreted via web interface 240 or voice communications interface 242. Illustrative networks include, but are not limited to: a local network such as a USB network; a business' local area network; or a wide area network such as the Internet. User interface adapter 232 may be used to connect a keyboard 244, microphone 246, pointer device 248, speaker 250 and other user interface devices such as a touch-pad and/or a touch screen (not shown). Display adapter 234 may be used to connect display 204 and printer 252. Processor 222 may include any programmable control device. Processor 222 may also be implemented as a custom designed circuit that may be embodied in hardware devices such as application specific integrated circuits (ASICs) and field programmable gate arrays (FPGAs). The CP computer 202 may have resident thereon any desired operating system.

While the above processes have been described in terms of their performance on a CP computer 202, it will be understood that the processes can also be performed on a different type of device such as the remote controller 40. In addition, various portions of the described processes can be performed on the neurostimulator itself. In such an arrangement, the different type of device or the neurostimulator may include various ones of the components described with respect to FIG. 26 to perform the processes.

While the target stimulation field has been described as being represented by a linear tripole, it will be understood that other target field types are also possible. For example, the center point of stimulation and focus can be used to specify a target bipole in which the center point of stimulation lies at the midpoint between the target cathode and target anode, which are the specified focus distance apart. Moreover, the user inputs may include additional or different parameters and the target field may include different numbers of target poles that enable the target field to be further customized. As will be understood, the types of target fields that might be created are essentially limitless. Regardless of the type, however, the target field can be created to be substantially parallel with the trajectory of the dorsal root that is nearest to the specified center point of stimulation. In this regard, the target field may be considered to be substantially parallel with the a dorsal root trajectory when a path through its target poles or about which its target poles are symmetrical is substantially parallel with the dorsal root trajectory. As used herein, the term parallel is intended to encompass a line or curve that lies directly on the a dorsal root trajectory.

While the target field construction process is described above in terms of determining an electrode configuration that causes the stimulation field to be substantially parallel with the dorsal root trajectory, it will be understood that this refers to the attempt to determine an electrode configuration that best matches a target field that is substantially parallel with the dorsal root trajectory. The locations of the physical electrodes may not enable the resulting stimulation field to be perfectly parallel with the dorsal root trajectory.

While the invention herein disclosed has been described by means of specific embodiments and applications thereof, numerous modifications and variations could be made thereto by those skilled in the art without departing from the scope of the invention set forth in the claims.

What is claimed is:

1. A system comprising:
a neurostimulator that is connectable to a plurality of electrodes that are implantable in the spinal column of a patient; and
an external device that is configured to:
cause a first one or more of the plurality of electrodes to provide stimulation to the patient's neural tissue;
cause a second one or more of the plurality of electrodes to record neural responses evoked in the patient's neural tissue by the stimulation;
use the recorded neural responses to determine a trajectory of each of one or more dorsal roots of the patient;
receive one or more inputs that are associated with a desired location of a stimulation field that is to be generated by the neurostimulator and which is configured to provide pain relief to the patient;
determine an electrode configuration that causes the stimulation field to be substantially parallel with the trajectory of the dorsal root that is nearest to the desired location of the stimulation field; and communicate the electrode configuration to the neurostimulator.

2. The system of claim 1, wherein the external device is configured to determine the trajectory of each of the one or more dorsal roots of the patient by:
after the neurostimulator provides stimulation at each of a plurality of sample stimulation locations, determining a measurement of a neural response to the stimulation at each of the plurality of sample stimulation locations; and
determining the trajectory of each of the one or more dorsal roots based on the measured neural response to the stimulation at each of the plurality of sample stimulation locations.

3. The system of claim 2, wherein the neural response to the stimulation at each of the plurality of sample stimulation locations is measured based on one or more properties of an evoked compound action potential (ECAP) at one or more of the plurality of electrodes.

4. The system of claim 2, wherein the external device is configured to generate a neural response map that comprises a metric of the measured neural response at each of the plurality of sample stimulation locations.

5. The system of claim 4, wherein determining the trajectory of each of the one or more dorsal roots based on the neural response to stimulation at the plurality of sample stimulation locations comprises performing a mathematical operation on the metric over the neural response map.

6. The system of claim 1, wherein the external device is configured to determine the trajectory of each of the one or more dorsal roots of the patient by:
after the neurostimulator provides stimulation at each of a plurality of sample stimulation locations, determining a stimulation amplitude at which the patient perceives the stimulation at each of the plurality of sample stimulation locations; and
determining the trajectory of each of the one or more dorsal roots based on the stimulation amplitude at which the patient perceives the stimulation at each of the plurality of sample stimulation locations.

7. The system of claim 6, wherein the neurostimulator provides stimulation at each of the plurality of sample stimulation locations at increasing stimulation amplitudes until the patient perceives the stimulation.

8. The system of claim 6, wherein the external device is configured to generate a patient response map based on the stimulation amplitude at which the patient perceives the stimulation at each of the plurality of sample stimulation locations.

9. The system of claim 8, wherein determining the trajectory of each of the one or more dorsal roots based on the stimulation amplitude at which the patient perceives the stimulation at each of the plurality of sample stimulation locations comprises performing a mathematical operation on the stimulation amplitude over the patient response map.

10. The system of claim 1, wherein the one or more inputs comprise a center point of the stimulation field.

11. The system of claim 1, wherein the one or more inputs comprise a focus of the stimulation field.

12. The system of claim 1, wherein the external device is configured to determine the electrode configuration that causes the stimulation field to be substantially parallel with the trajectory of the dorsal root that is nearest to the desired location of the stimulation field by:
determining a location of one or more target poles based on the one or more inputs, wherein the target poles are aligned with or symmetrical about a path that is substantially parallel with the trajectory of the dorsal root that is nearest to the desired location of the stimulation field;
estimating an electric field that would result from stimulation at the one or more target poles; and
determining the electrode configuration that corresponds to the estimated electric field.

13. The system of claim 12, wherein the one or more target poles comprise a target cathode at a center point of the stimulation field and two equal target anodes that are each positioned at an equal distance from the center point of stimulation along the path.

14. The system of claim 1, wherein the electrode configuration specifies a polarity and magnitude of stimulation for the plurality of electrodes.

15. The system of claim 1, wherein the external device is further configured to:
determine an electric field that would result from stimulation using the electrode configuration;
determine a response of neural elements to the electric field at a plurality of neural element evaluation positions, wherein the neural element evaluation positions comprise positions that are substantially parallel with the trajectory of each of the one or more dorsal roots; and
adjust the electrode configuration if the determined response of neural elements deviates from a desired response.

16. The system of claim 15, wherein the external device is further configured to estimate a location of one or more dorsal root ganglia based, at least in part, on the trajectory of each of the one or more dorsal roots of the patient.

17. A method of providing stimulation to patient, wherein the patient is implanted with a plurality of electrodes in their spinal column, wherein the plurality of electrodes are connectable to a neurostimulator, the method comprising:
using a first one or more of the plurality of electrodes to provide stimulation to the patient's neural tissue;
using a second one or more of the plurality of electrodes to record neural responses evoked in the patient's neural tissue by the stimulation;
using the recorded neural responses to determine a trajectory of each of one or more dorsal roots of the patient;
receiving one or more inputs that are associated with a desired location of a stimulation field that is to be generated by the neurostimulator and which is configured to provide pain relief to the patient;
determining an electrode configuration that causes the stimulation field to be substantially parallel with the trajectory of the dorsal root that is nearest to the desired location of the stimulation field; and
communicating the electrode configuration to the neurostimulator.

18. The method of claim 17, wherein determining the trajectory of each of the one or more dorsal roots comprises:
providing stimulation at each of a plurality of sample stimulation locations;
determining a measurement of a neural response to the stimulation at each of the plurality of sample stimulation locations; and
determining the trajectory of each of the one or more dorsal roots based on the measured neural response to the stimulation at each of the plurality of sample stimulation locations.

19. The method of claim 17, wherein determining the trajectory of each of the one or more dorsal roots comprises:

providing stimulation at each of a plurality of sample stimulation locations;

determining a stimulation amplitude at which the patient perceives the stimulation at each of the plurality of sample stimulation locations; and determining the trajectory of each of the one or more dorsal roots based on the stimulation amplitude at which the patient perceives the stimulation at each of the plurality of sample stimulation locations.

20. The method of claim 17, wherein determining the electrode configuration that causes the stimulation field to be substantially parallel with the trajectory of the dorsal root comprises:

determining a location of one or more target poles based on the one or more inputs, wherein the target poles are aligned with or symmetrical about a path that is substantially parallel with the trajectory of the dorsal root that is nearest to the desired location of the stimulation field;

estimating an electric field that would result from stimulation at the one or more target poles; and determining the electrode configuration that corresponds to the estimated electric field.

* * * * *